US010413307B2

(12) United States Patent
Chaney et al.

(10) Patent No.: US 10,413,307 B2
(45) Date of Patent: Sep. 17, 2019

(54) FEMORAL ORTHOPAEDIC INSTRUMENT ASSEMBLY FOR SETTING OFFSET

(71) Applicant: DEPUY IRELAND UNLIMITED COMPANY, Co Cork (IE)

(72) Inventors: Rebecca L. Chaney, Warsaw, IN (US); Craig S. Tsukayama, Fort Wayne, IN (US); Joseph G. Wyss, Warsaw, IN (US)

(73) Assignee: DEPUY IRELAND UNLIMITED COMPANY, Ringaskiddy, Co Cork (IE)

( * ) Notice: Subject to any disclaimer, the term of this patent is extended or adjusted under 35 U.S.C. 154(b) by 24 days.

(21) Appl. No.: 15/584,654

(22) Filed: May 2, 2017

(65) Prior Publication Data

US 2017/0231642 A1 Aug. 17, 2017

Related U.S. Application Data

(63) Continuation of application No. 13/832,194, filed on Mar. 15, 2013, now Pat. No. 9,636,122.

(51) Int. Cl.
*A61B 17/15* (2006.01)
*A61B 17/17* (2006.01)
*A61B 17/16* (2006.01)

(52) U.S. Cl.
CPC ........ *A61B 17/1764* (2013.01); *A61B 17/155* (2013.01); *A61B 17/1675* (2013.01); *A61B 17/164* (2013.01)

(58) Field of Classification Search
CPC ....................... A61F 2/389; A61F 2/461; A61F 2002/30594; A61F 2002/30887; A61F 2002/30897; A61B 17/1764; A61B 17/921
See application file for complete search history.

(56) References Cited

U.S. PATENT DOCUMENTS

| 4,791,919 A | 12/1988 | Elloy |
| 5,356,414 A | 10/1994 | Cohen et al. |
| 5,662,656 A * | 9/1997 | White ................. A61B 17/155 606/86 R |
| 5,681,316 A | 10/1997 | Deorio et al. |
| 6,077,270 A | 6/2000 | Katz |
| 7,175,633 B2 | 2/2007 | Roth |

(Continued)

FOREIGN PATENT DOCUMENTS

| CN | 101827560 A | 9/2010 |
| CN | 101835441 A | 9/2010 |

(Continued)

OTHER PUBLICATIONS

European Search Report for European Application No. 14158601. 6-1654, dated Jun. 12, 2014, 7 pages.

(Continued)

*Primary Examiner* — Matthew J Lawson
(74) *Attorney, Agent, or Firm* — Barnes & Thornburg LLP

(57) ABSTRACT

A number of orthopedic surgical instruments for use in a surgical procedure to prepare a patient's femur to receive an orthopedic prosthesis. The tools include guide tools, cutting tools, surgical blocks, and other orthopedic surgical instruments configured to plan and guide the preparation of the patient's femur. A method of using the orthopedic surgical instruments is also disclosed.

6 Claims, 30 Drawing Sheets

(56) References Cited

U.S. PATENT DOCUMENTS

| | | | |
|---|---|---|---|
| 7,497,874 B1 | 3/2009 | Metzger et al. | |
| 8,394,103 B2 | 3/2013 | O'Reilly | |
| 8,597,298 B2 | 12/2013 | Daniels | |
| 9,636,122 B2 | 5/2017 | Chaney et al. | |
| 2008/0091273 A1 | 4/2008 | Hazebrouck | |
| 2008/0177337 A1 | 7/2008 | McGovern et al. | |
| 2008/0183177 A1 | 7/2008 | Fox et al. | |
| 2009/0125114 A1* | 5/2009 | May et al. | A61B 17/1764 623/20.14 |
| 2009/0149964 A1* | 6/2009 | May | A61B 17/155 623/20.15 |
| 2009/0204115 A1 | 8/2009 | Dees, Jr. | |
| 2009/0222008 A1 | 9/2009 | Hogg et al. | |
| 2009/0306787 A1* | 12/2009 | Crabtree | A61F 2/4684 623/20.34 |
| 2012/0156479 A1 | 6/2012 | Nakamura et al. | |
| 2012/0310246 A1 | 12/2012 | Belcher et al. | |
| 2013/0172892 A1* | 7/2013 | Servidio | A61B 17/1717 606/80 |
| 2013/0325014 A1* | 12/2013 | Sordelet | A61B 17/155 606/82 |
| 2013/0325016 A1 | 12/2013 | Sordelet et al. | |
| 2013/0325018 A1 | 12/2013 | Thomas et al. | |
| 2013/0325019 A1 | 12/2013 | Thomas et al. | |
| 2013/0325021 A1 | 12/2013 | Sordelet et al. | |
| 2013/0325136 A1* | 12/2013 | Thomas | A61B 17/157 623/20.32 |
| 2014/0276858 A1* | 9/2014 | Major | A61B 17/157 606/88 |

FOREIGN PATENT DOCUMENTS

| | | |
|---|---|---|
| EP | 2145590 A | 1/2010 |
| EP | 2145590 A1 | 1/2010 |
| FR | 2748389 A1 | 11/1997 |
| FR | 2752519 A1 | 2/1998 |
| FR | 2943528 A1 | 10/2010 |
| GB | 2323037 A | 9/1998 |
| JP | S61209654 | 9/1986 |
| JP | 2005529628 | 10/2005 |
| JP | 2009509716 | 3/2009 |
| JP | 2012213661 A | 11/2012 |
| WO | 1998052499 A1 | 11/1998 |
| WO | 0013597 A1 | 3/2000 |
| WO | 2007114841 A1 | 10/2007 |
| WO | 2010019284 A1 | 2/2010 |

OTHER PUBLICATIONS

Zimmer NexGen LCCK, Surgical Technique for use with LCCK 4-in-1 Instrument, 2009, 52 pages.
DePuy Orthopaedics, Inc., Sigma Revision and M.B.T. Revision Tray, Surgical Technique, 2008, 82 pages.
Smith & Nephew, Legion, Revision Knee System, Surgical Technique, 2005, 40 pages.
Biomet, Vanguard SSK, Revision System, Surgical Technique, Feb. 2008, 64 pages.
LCS High Performance Instruments, Surgical Technique, 2008, 44 pages.
Sigma High Performance Instruments, Design Rationale, 2007, 12 pages.
Sigma High Performance Instruments, Classic Surgical Technique, 2010, 52 pages.
Attune Knee System Surgical Technique, 2013, 73 pages.
PFC Sigma RP-F, Specialist 2 Instruments, Surgical Technique, Performance in Flexion, 2007, 32 pages.
P.F.C. Sigma Rotating Platform Knee System with M.B.T. Tray, Primary Procedure with a Curved or Posterior Stabilized Implant, 2003, 43 pages.
European Search Report, European Patent Application No. 14158601.6-1654 / 2777550, dated Oct. 24, 2014, 10 pages.
English translation of Chinese First Office Action, Chinese Application No. 201410095526.2, dated Apr. 11, 2017, 6 pages.
GMK Revision, Surgical Technique, Ref 99.27.12US rev. 1, 74 pages (1999).

* cited by examiner

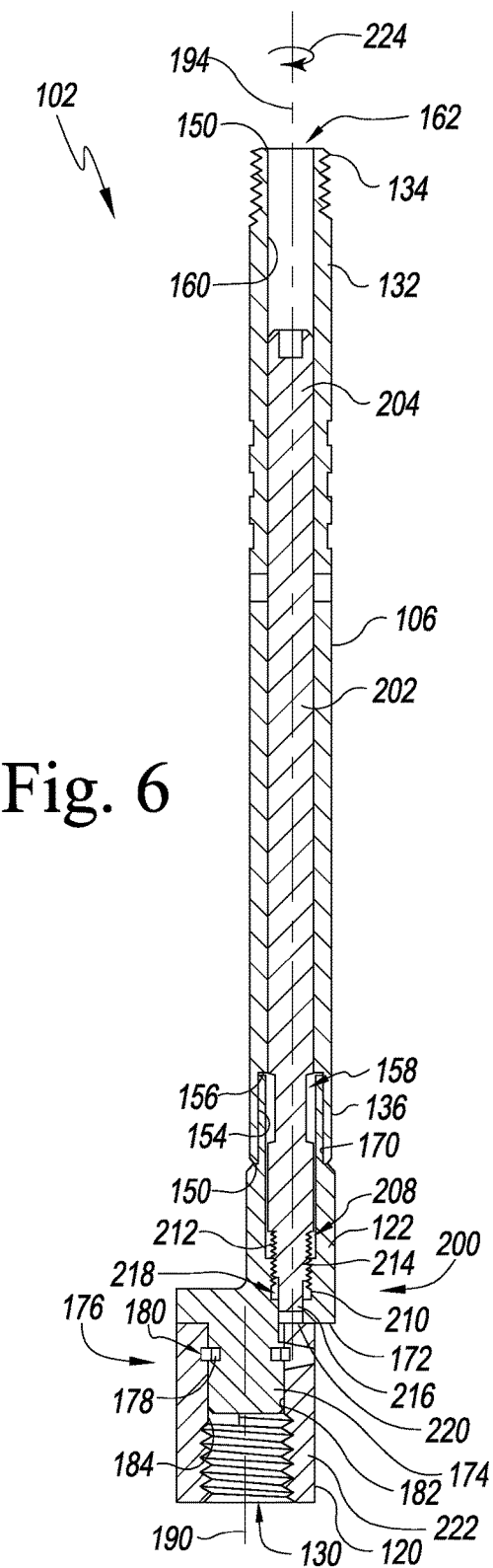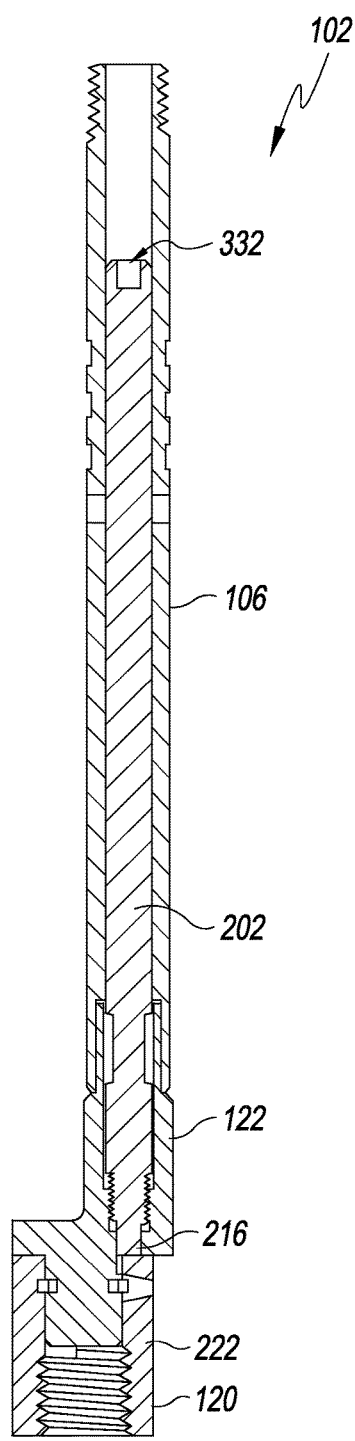
Fig. 6
Fig. 7

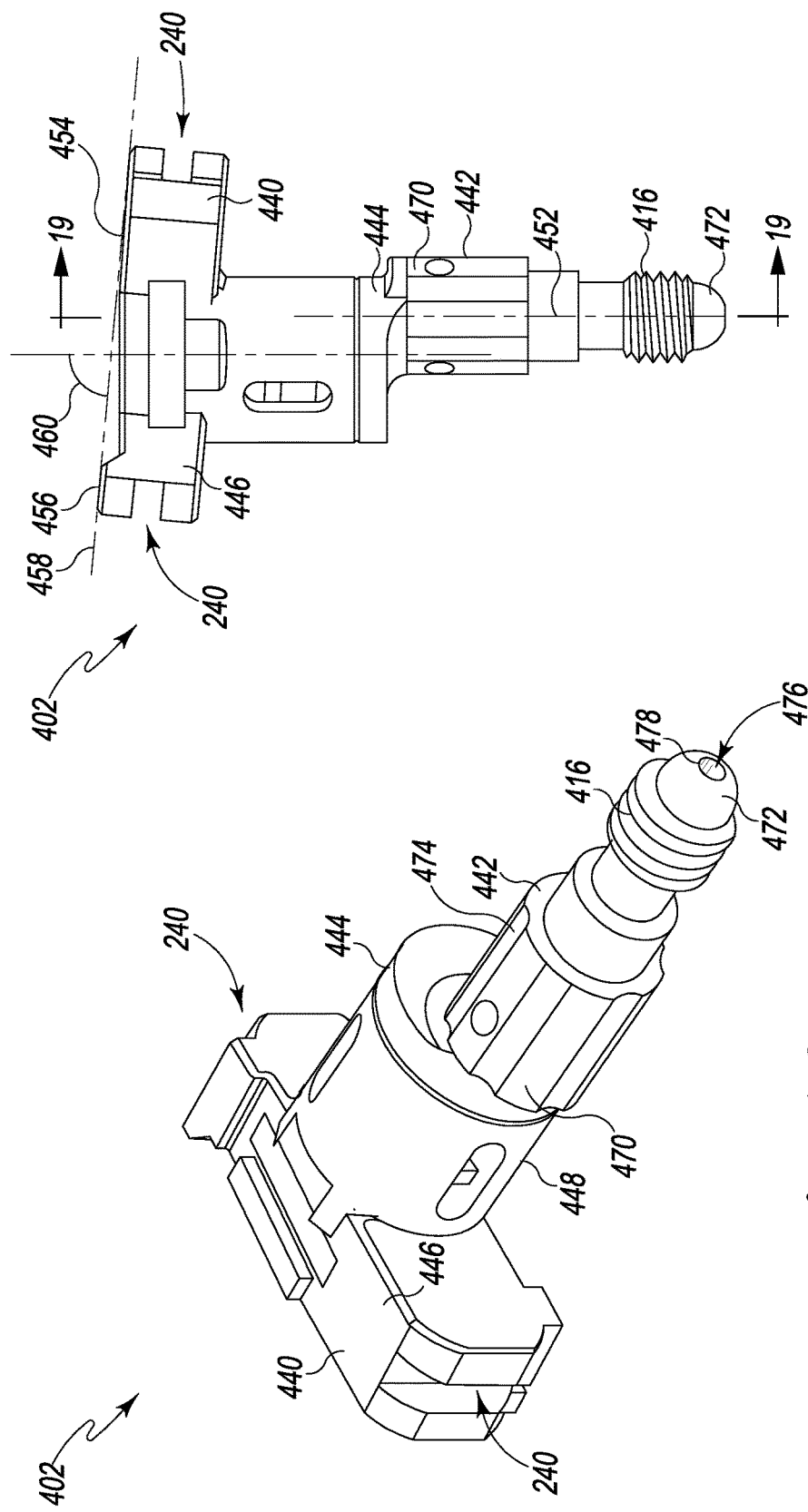

FEMORAL ORTHOPAEDIC INSTRUMENT ASSEMBLY FOR SETTING OFFSET

CROSS-REFERENCE

This application is a continuation of U.S. patent application Ser. No. 13/832,194, now U.S. Pat. No. 9,636,122 entitled "FEMORAL ORTHOPAEDIC INSTRUMENT ASSEMBLY FOR SETTING OFFSET" and having a filing date of Mar. 15, 2013, which is herein incorporated by reference in its entirety.

Cross reference is made to copending U.S. patent application Ser. No. 13/832,203 entitled "FEMORAL ORTHOPAEDIC SURGICAL INSTRUMENTS FOR SETTING OFFSET"; and copending U.S. patent application Ser. No. 13/832,183 entitled "METHOD OF SURGICALLY PREPARING A PATIENT'S FEMUR", each of which is assigned to the same assignee as the present application, each of which is filed concurrently herewith, and each of which is hereby incorporated by reference.

TECHNICAL FIELD

The present disclosure relates generally to orthopaedic instruments for use in the performance of an orthopaedic joint replacement procedure, and more particularly to orthopaedic surgical instruments for use in the performance of a knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis is surgically removed and a replacement knee prosthesis is implanted. In some revision knee surgeries, all of the components of the previously-implanted knee prosthesis, including, for example, the tibial tray, the femoral component, and the polymer bearing, may be surgically removed. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, surgical reamers, drill guides, prosthetic trials, and other surgical instruments to prepare the patient's bones to receive the knee prosthesis. Other orthopaedic surgical instruments such as trial components may be used to size and select the components of the knee prosthesis that will replace the patient's natural joint. Trial components may include a femoral trial that may be used to size and select a prosthetic femoral component, a tibial tray trial that may be used to size and select a prosthetic tibial tray, and a stem trial that may be used to size and select a prosthetic stem component.

SUMMARY

According to one aspect of the disclosure, a method of surgically preparing a patient's femur to receive an orthopaedic prosthesis is disclosed. The method includes attaching a stem trial to a proximal end of an offset tool, advancing the stem trial through a distal surface of the patient's femur into a distal end of a medullary canal, positioning a surgical block on a distal surface of the patient's femur, attaching the surgical block to a distal end of the offset tool, rotating the distal end of the offset tool relative to the stem trial to move the surgical block on the distal surface of the patient's femur, and preventing rotation of the distal end of the offset tool when the surgical block is in a desired offset orientation, advancing a cannulated reamer over the distal end of the offset tool. The method also includes reaming the patient's femur with the cannulated reamer to define a chamber at the distal end of the medullary canal, removing the stem trial from the medullary canal, and inserting an intramedullary orthopaedic surgical instrument into the chamber and the medullary canal of the patient's femur. The intramedullary orthopaedic surgical instrument includes the stem trial.

In some embodiments, attaching the surgical block to the distal end of the offset tool may include advancing a guide block over the distal end of the offset tool, and positioning a locking pin of the guide block in a slot defined in the surgical block. Additionally, attaching the surgical block to the distal end of the offset tool may include rotating a tab of the surgical block into a channel defined in the mounting bracket of the guide block.

In some embodiments, the method may include selecting a first slot of a plurality of slots defined in the distal end of the offset tool. Each slot may correspond to a desired reaming depth. The method may also include engaging the first slot with a locking tab of the guide block.

In some embodiments, reaming the patient's femur with the cannulated reamer may include identifying a depth indicator on the cannulated reamer corresponding to the desired reaming depth, and advancing the cannulated reamer into the patient's femur until the depth indicator is coplanar with the distal surface of the patient's femur.

In some embodiments, the method may include attaching a handle to the distal end of the offset tool after attaching the surgical block to the offset tool, and rotating the distal end of the offset tool may include gripping the handle to rotate the distal end of the offset tool.

In some embodiments, preventing rotation of the distal end of the offset tool may include engaging a connecting shaft that is moveably coupled to the handle, and rotating the connecting shaft relative to the handle to operate a locking mechanism of the offset tool.

In some embodiments, the method may include securing the intramedullary orthopaedic surgical instrument to an intramedullary adaptor, positioning a first adaptor body of the intramedullary adaptor relative to a second adaptor body of the intramedullary adaptor based on the desired offset orientation, and locking the first adaptor body in position relative to the second adaptor body.

Additionally, the method may include identifying a first offset indicator when the surgical block is in the desired offset orientation. The first offset indicator may correspond to the desired offset orientation. The method may also include identifying a second offset indicator on the intramedullary adaptor corresponding to the desired offset orientation, and positioning the first adaptor body of the intramedullary adaptor relative to the second adaptor body of the intramedullary adaptor based on the desired offset orientation may include rotating the first adaptor body of the intramedullary adaptor relative to the second adaptor body to a position associated with the second offset indicator.

In some embodiments, securing the intramedullary orthopaedic surgical instrument to the intramedullary adaptor may include securing a distal end of the stem trial to a proximal end of a stem stabilizer and securing the distal end of the stem stabilizer to a proximal end of the intramedullary adaptor.

In some embodiments, the method may include positioning a mounting bracket of the intramedullary adaptor in a slot defined the surgical block, and advancing a tab of the surgical block into a channel defined in the mounting bracket to secure the intramedullary adaptor to the surgical block. Additionally, the method may include operating a locking mechanism of the intramedullary adaptor to permit the mounting bracket to rotate relative to the first adaptor body, and rotating the mounting bracket and the surgical block on the distal surface of the patient's femur relative to the first adaptor body. In some embodiments, the surgical block used in the method may include a cutting guide slot configured to guide a surgical saw during a resection of a posterior surface of the patient's femur.

According to another aspect, a method for performing an orthopaedic surgical procedure on a patient's femur includes securing a distal end of an intramedullary orthopaedic surgical instrument to a proximal end of an intramedullary adaptor, rotating a first adaptor body of the intramedullary adaptor to a desired offset orientation relative to a second adaptor body of the intramedullary adaptor, advancing the intramedullary orthopaedic surgical instrument and the proximal end of the intramedullary adaptor through a distal surface of the femur, and positioning a surgical block secured to the distal end of the intramedullary adaptor on the distal surface of the femur.

In some embodiments, the method may include positioning a mounting bracket of the intramedullary adaptor in a slot defined the surgical block and advancing a tab of the surgical block into a channel defined in the mounting bracket to secure the intramedullary adaptor to the surgical block.

In some embodiments, the surgical block may include a cutting guide slot configured to guide a surgical saw during a resection of a posterior surface of the patient's femur.

In some embodiments, the method may include attaching a stem trial to a proximal end of an offset tool, advancing the stem trial and the proximal end of the offset tool through the distal surface of the patient's femur into a distal end of a medullary canal, and rotating a distal end of the offset tool relative to the stem trial to identify the desired offset orientation.

In some embodiments, the method may include advancing a cannulated reamer over the distal end of the offset tool when the distal end is positioned in the desired offset orientation, and reaming the patient's femur with the cannulated reamer.

According to another aspect, a method for performing an orthopaedic surgical procedure on a patient's femur includes positioning an intramedullary orthopaedic surgical instrument in a medullary canal of the patient's femur, positioning a reamer guide assembly on a distal surface of the patient's femur in a desired offset orientation relative to the intramedullary orthopaedic surgical instrument, advancing a cannulated reamer over a shaft of the reamer guide assembly to ream the patient's femur at the desired offset orientation, removing the intramedullary orthopaedic surgical instrument from the medullary canal of the patient's femur after reaming, and securing the intramedullary orthopaedic surgical instrument to a proximal end of an intramedullary adaptor. The method also includes positioning a first adaptor body of the intramedullary adaptor relative to a second adaptor body of the intramedullary adaptor based on the desired offset orientation, inserting the intramedullary orthopaedic surgical instrument and the proximal end of the intramedullary adaptor into the patient's femur, and operating a locking mechanism to permit a distal end of the intramedullary adaptor to rotate relative to the first adaptor body.

In some embodiments, positioning the reamer guide assembly on the distal surface of the patient's femur may include locating a surgical block that includes a cutting guide slot configured to guide a surgical saw during a resection of a posterior surface of the patient's femur on the distal surface in the desired offset orientation, and inserting the intramedullary orthopaedic surgical instrument and the proximal end of the intramedullary adaptor into the patient's femur may include locating the surgical block on the distal surface in the desired offset orientation. The surgical block may be secured to the distal end of the intramedullary adaptor.

According to one aspect of the disclosure, an orthopaedic surgical instrument assembly is disclosed. The instrument assembly includes a cutting block including a base plate and a pair of curved arms extending posteriorly from the base plate. Each curved arm includes a posterior surface and a cutting guide defined in the posterior surface. The instrument assembly also includes a stem trial positioned proximal to the base plate of the cutting block, and an offset tool having a proximal end coupled to the stem trial and a distal end coupled to the cutting block. The proximal end of the offset tool defines a first axis, and the distal end of the offset tool defines a second axis extending parallel to the first axis. The proximal end of the offset tool is configured to pivot relative to the distal end.

In some embodiments, the instrument assembly may include a guide block including a mounting bracket engaged with the base plate. The offset tool may include a shaft extending through a cylindrical passageway defined in the guide block. Additionally, the cutting block may include a tab that is pivotal between a first position in which the tab is engaged with the mounting bracket to secure the guide block to the cutting block, and a second position in which the tab is disengaged from the mounting bracket such that the guide block is removable from the cutting block.

In some embodiments, the guide block may include a locking mechanism configured to secure the guide block to the shaft of the offset tool. In some embodiments, the shaft of the offset tool may include a plurality of slots. Each slot may correspond to a predetermined reaming depth, and the locking mechanism of the guide block may include a locking pin that is moveable between a first position in which the locking pin is positioned in one of the plurality of slots to secure the guide block to the shaft of the offset tool, and a second position in which the locking pin is disengaged from the plurality of slots such that the guide block is removable from the shaft.

Additionally, in some embodiments, the offset tool may include a locking mechanism configured to prevent rotation of the distal end relative to the proximal end. The shaft of the offset tool may be a first shaft including the proximal end of the offset tool, and the offset tool may include a connecting body extending between the first shaft and a second shaft. The second shaft may include the distal end of the offset tool. The locking mechanism may include a threaded rod positioned in a passageway defined in the first shaft. The threaded rod may be moveable along the first axis between a first position in which the threaded rod is spaced apart from the connecting body such that relative movement between the first shaft and the second shaft is permitted, and a second position in the threaded rod is engaged with the connecting body such that relative movement between the first shaft and the second shaft is prevented.

In some embodiments, the instrument assembly may further include a handle engaged with the distal end of the first shaft. A connecting rod may be pivotally coupled to the handle, and the connecting rod may have a driver head configured to be engaged with a distal end of the threaded rod. In some embodiments, the handle may include a plurality of internal threads that engage a plurality of external threads formed on the distal end of the shaft.

In some embodiments, the instrument assembly may further include an indicator to indicate a position of the proximal end relative to the distal end of the offset tool. Additionally, in some embodiments, the instrument assembly may further include a cannulated reamer sized to receive a shaft of the offset tool.

According to another aspect, an orthopaedic surgical instrument assembly includes a surgical block having a proximal surface, a distal surface opposite the proximal surface, and a slot extending through the proximal surface and the distal surface. The instrument assembly also includes a guide block including a mounting bracket positioned in the slot and removably coupled to the surgical block, an offset tool including a first shaft that extends through a cylindrical passageway defined in the guide block and defines a first axis and a second shaft pivotally coupled to the first shaft. A stem trial is secured to the second shaft of the offset tool. An oblique angle is defined between the first axis and an imaginary plane defined by the proximal surface of the surgical block.

In some embodiments, the instrument assembly may further include a rod coupled to the first shaft. The rod may be moveable along the first axis between a first position in which the first shaft is permitted to rotate relative to the second shaft and a second position in which the first shaft is prevented from rotating relative to the second shaft.

In some embodiments, the instrument assembly may include a handle secured to the first shaft, and a connecting rod moveably coupled to the handle. The connecting rod may have a driver head engaged with a distal end of the rod.

In some embodiments, the surgical block may include a base plate having the slot defined therein and a pair of curved arms extending posteriorly from the base plate. Each curved arm may include a posterior surface and a cutting guide defined in the posterior surface. In some embodiments, the instrument assembly may include a cannulated reamer including an aperture sized to receive a shaft of the offset tool.

In some embodiments, the first shaft of the offset tool may include a plurality of slots, and each slot may correspond to a predetermined reaming depth of the cannulated reamer. The guide block may include a locking pin that is moveable between a first position in which the locking pin is positioned in one of the plurality of slots to secure the guide block to the first shaft of the offset tool and a second position in which the locking pin is disengaged from the plurality of slots such that the guide block is removable from the first shaft.

According to another aspect, an orthopaedic surgical instrument assembly includes an offset tool and a stem trial. The offset tool includes a first shaft defining a first axis, a second shaft pivotally coupled to the first shaft, and a locking mechanism configured to prevent relative movement between the first shaft and the second shaft. The stem trial is secured to the second shaft of the offset tool. The stem trial includes an elongated body that defines a second axis extending parallel to the first axis. The instrument assembly also includes a cannulated reamer including an aperture sized to receive the first shaft of the offset tool.

In some embodiments, the offset tool may include a connecting body extending between the first shaft and the second shaft, and the locking mechanism may include a rod coupled to the first shaft. The rod may be moveable along the first axis between a first position in which a tip of the rod is spaced apart from the connecting body such that relative movement between the first shaft and the second shaft is permitted and a second position in which the tip is engaged with the connecting body such that relative movement between the first shaft and the second shaft is prevented.

In some embodiments, the instrument assembly further includes a handle secured the shaft, and a connecting shaft moveably coupled to the handle. The connecting shaft may be operable to move the rod between the first position and the second position.

According to another aspect, an orthopaedic surgical instrument assembly includes a cutting block and an intramedullary orthopaedic surgical instrument. The cutting block includes a base plate, and a pair of curved arms extending posteriorly from the base plate. Each curved arm includes a posterior surface and a cutting guide defined in the posterior surface. The intramedullary orthopaedic surgical instrument is configured to be inserted into a medullary canal of a patient's femur. The instrument assembly also includes an adaptor positioned in a slot defined in the base plate. The adaptor includes a mounting bracket engaged with the base plate, a first adaptor body coupled to the mounting bracket, and a second adaptor body pivotally coupled to the first adaptor body. The second adaptor body includes a fastener coupled to the intramedullary orthopaedic surgical instrument. The first adaptor body defines a first axis, the intramedullary orthopaedic surgical instrument includes an elongated body that defines a second axis extending parallel to the first axis, and when the second adaptor body is pivoted relative to the first adaptor body, the elongated body is pivoted about the first axis.

In some embodiments, the intramedullary orthopaedic surgical instrument may include a stem trial including the elongated body and an externally-threaded end, and a stem stabilizer including a second elongated body. The second elongated body has an internally-threaded first end engaged with the externally-threaded end of the stem trial and an internally-threaded second end positioned opposite the first end. The second end may be engaged with a threaded shaft of the fastener of the adaptor.

In some embodiments, the mounting bracket may include a distal surface that defines an imaginary plane. An oblique angle may be defined between the first axis of the first adaptor body and the imaginary plane.

In some embodiments, the adaptor may include a locking mechanism configured to prevent relative movement between the second adaptor body and the first adaptor body. Additionally, the locking mechanism may include a threaded pin coupled to the first adaptor body. The threaded pin may be moveable between a first position in which a tip of the threaded pin engages the second adaptor body to prevent relative movement between the second adaptor body and the first adaptor body and a second position in which the tip of the threaded pin is disengaged from the second adaptor body to permit relative movement between the second adaptor body and the first adaptor body.

In some embodiments, the first adaptor body may have a passageway extending along the first axis of the first adaptor body to a proximal end and an aperture defined at the proximal end. The threaded pin may be positioned in the aperture.

In some embodiments, the mounting bracket may be pivotally coupled to the first adaptor body, and the adaptor may include a locking mechanism configured to prevent relative movement between the mounting bracket and the first adaptor body.

Additionally, in some embodiments, the locking mechanism may include a threaded insert attached to a distal end of the first adaptor body. When the threaded insert is rotated in a first direction, an annular flange of the first adaptor body may be moved along the first axis into engagement with a proximal surface of the mounting bracket such that relative movement between the first adaptor body and the mounting bracket is prevented. When the threaded insert is rotated in a second direction, the annular flange of the first adaptor body may be moved along the first axis away from the proximal surface of the mounting bracket such that relative movement between the first adaptor body and the mounting bracket is permitted.

In some embodiments, the cutting block may include a tab pivotally coupled to the base plate. The tab may be moveable between a first position in which the tab is engaged with the mounting bracket to secure the adaptor to the cutting block, and a second position in which the tab is disengaged from the mounting bracket such that the adaptor is removable from the cutting block.

In some embodiments, the instrument assembly may include a guide block configured to be positioned in the slot of the base plate in place of the adaptor. The guide block may include a mounting bracket configured to engage with the cutting block and a cylindrical passageway defined therein sized to receive an orthopaedic surgical instrument.

According to another aspect, an orthopaedic surgical instrument assembly includes a mounting bracket including a main housing and a pair of arms extending outwardly from the main housing. Each arm has a slot defined therein sized to receive a locking tab of a surgical block. The instrument assembly also includes a first body pivotally coupled to a proximal end of the main housing of the mounting bracket. The first body defines a first longitudinal axis. A second body is pivotally coupled to a proximal end of the first body. The second body is configured to be coupled to an orthopaedic intramedullary adaptor and defines a second longitudinal axis extending parallel to the first longitudinal axis. The mounting bracket includes a distal surface that defines an imaginary plane, and an oblique angle is defined between the imaginary plane and the first longitudinal axis.

In some embodiments, the instrument assembly may include an intramedullary orthopaedic surgical instrument secured to a distal end of the second body. The intramedullary orthopaedic surgical instrument may include a stem trial configured to be inserted into a medullary canal of a patient's femur.

In some embodiments, the stem trial may include an externally-threaded distal end. The intramedullary orthopaedic surgical instrument may include a stem stabilizer including an internally-threaded first end engaged with the externally-threaded distal end of the stem trial and an internally-threaded second end positioned opposite the first end, the second end being engaged with an externally-threaded end of the second body.

In some embodiments, the instrument assembly may include a first locking mechanism configured to prevent relative movement between the mounting bracket and the first body, and a second locking mechanism configured to prevent relative movement between the second body and the first body.

Additionally, the first body may have a threaded inner wall that defines passageway extending along the first longitudinal axis of the first body. The first locking mechanism may include an insert engaged with the threaded inner wall of the first body. When the insert is rotated in a first direction, an annular flange of the first body may be moved along the first longitudinal axis into engagement with a proximal surface of the mounting bracket such that relative movement between the first body and the mounting bracket is prevented. When the insert is rotated in a second direction, the annular flange of the first body may be moved along the first longitudinal axis away from the proximal surface of the mounting bracket such that relative movement between the first body and the mounting bracket is permitted.

In some embodiments, the first body may have an aperture positioned at a proximal end of the passageway, and the second locking mechanism may include a threaded pin positioned in the aperture of the first body. The threaded pin may be moveable between a first position in which a tip of the threaded pin engages the second body to prevent relative movement between the second body and the first body and a second position in which the tip of the threaded pin is disengaged from the second body to permit relative movement between the second body and the first body.

In some embodiments, the insert of the first locking mechanism may have a passageway extending therethrough. The passageway may be sized to permit a surgical tool to extend through to engage the threaded pin.

According to another aspect, an orthopaedic surgical instrument system includes a surgical block including a locking tab, and an adaptor configured to be positioned in a slot defined in the surgical block. The adaptor includes a mounting bracket configured to engage the locking tab to secure the adaptor to the surgical block, a first adaptor body coupled to the mounting bracket and defining a first axis, and a second adaptor body pivotally coupled to the first adaptor body. The second adaptor body defines a second axis offset from and extending parallel to the first axis. The instrument system also includes an offset tool including a first shaft that defines a third axis and a second shaft pivotally coupled to the first shaft. The second shaft defines a fourth axis offset from and extending parallel to the third axis. The instrument system includes a guide block configured to be positioned in the slot of the surgical block in place of the adaptor. The guide block includes a mounting bracket configured to engage the locking tab to secure the guide block to the surgical block and a cylindrical passageway defined therein sized to receive the first shaft of the offset tool. The second axis is offset from the first axis by a first distance, and the fourth axis offset from the third axis by a second distance equal to the first distance.

The surgical block may include a base plate having the slot defined therein and a pair of curved arms extending posteriorly from the base plate. Each curved arm may include a posterior surface and a cutting guide defined in the posterior surface.

In some embodiments, the instrument system may include a stem trial including a first elongated body and an externally-threaded end, and a stem stabilizer including a second elongated body. The second elongated body may have an internally-threaded first end configured to engage the externally-threaded end of the stem trial and an internally-threaded second end positioned opposite the first end. The second end may be engaged with a distal end of the adaptor. The offset tool may have an internally-threaded proximal end configured to engage the externally-threaded end of the stem trial.

BRIEF DESCRIPTION OF THE DRAWINGS

The detailed description particularly refers to the following figures, in which:

FIG. 6 is a cross-sectional elevation view taken along the line 6-6 in FIG. 4 showing an unlocked position of the offset guide tool;

FIG. 7 is a view similar to FIG. 6 showing a locked position of the offset guide tool;

FIG. 16 is a perspective view of an intramedullary adaptor of the instrument construct of FIG. 14;

FIG. 17 is an elevation view of the intramedullary adaptor of FIG. 16;

DETAILED DESCRIPTION OF THE DRAWINGS

Figure 1:
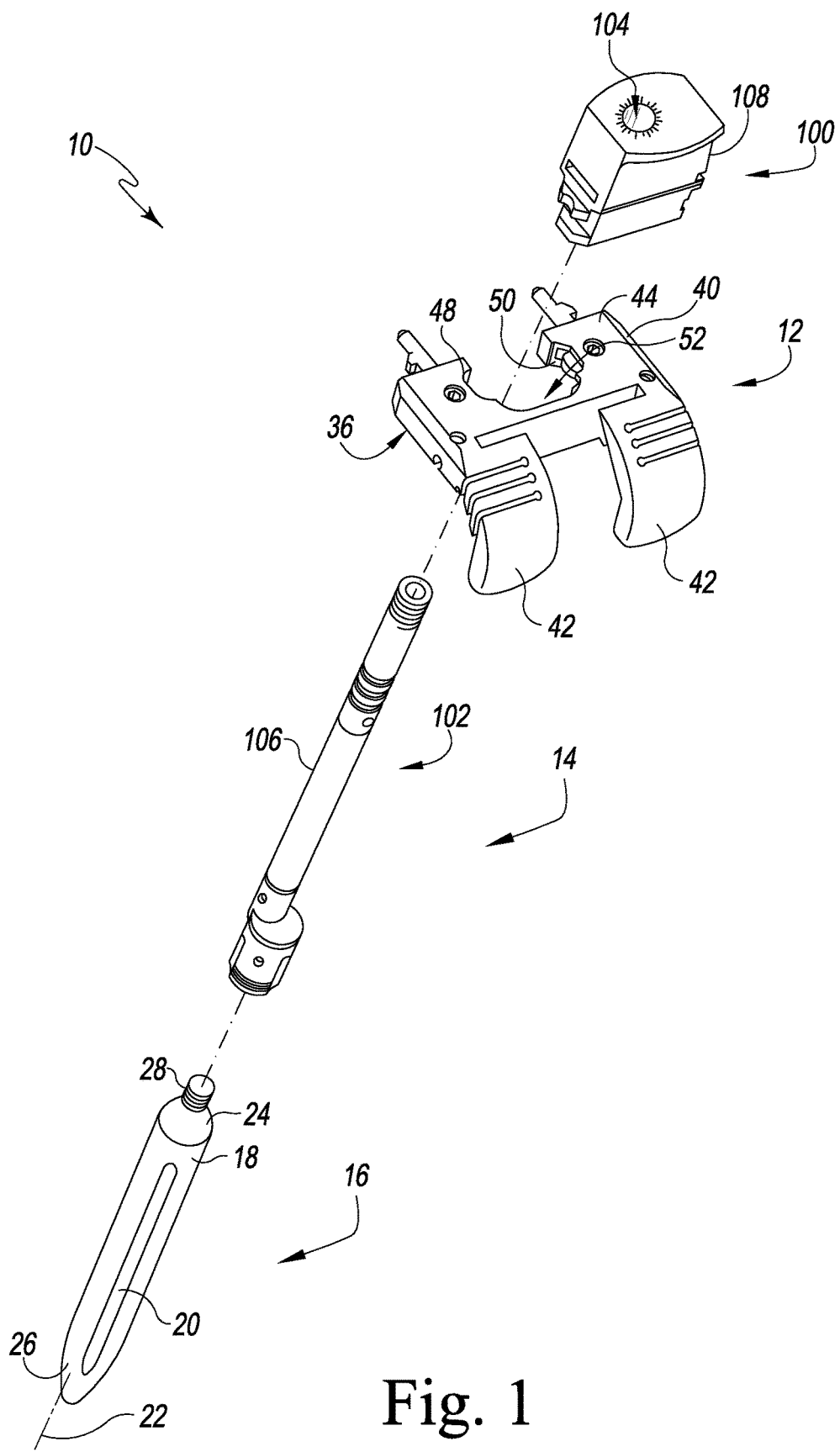
FIG. 1 is an exploded perspective view of a cutting block and an offset guide assembly of an orthopaedic surgical instrument system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIGS. 1-22, an orthopaedic surgical instrument system 10 (hereinafter instrument system 10) is shown. What is meant herein by the term "orthopaedic surgical instrument" or "orthopaedic surgical instrument system" is a surgical tool for use by a surgeon in performing an orthopaedic surgical procedure. As such, it should be appreciated that, as used herein, the terms "orthopaedic surgical instrument" and "orthopaedic surgical instruments" are distinct from orthopaedic implants or prostheses that are surgically implanted in the body of the patient. As described in greater detail below, the system 10 may be used to plan and guide the reaming of a distal end 622 of a patient's femur 620 (see FIG. 24) to receive an orthopaedic surgical instrument construct 400. When positioned on the patient's femur, the instrument construct 400 may be used to plan and guide the preparation of the distal end of the patient's femur to receive a femoral orthopaedic prosthesis 650 (see FIG. 23), as described in greater detail below.

The instrument system 10 includes a base cutting block 12 configured for use on a femur of a patient, and an offset guide assembly 14 configured to be secured to the base cutting block 12. The system 10 also includes an intramedullary orthopaedic surgical instrument 16 configured to be coupled to the offset guide assembly 14. What is meant herein by the term "intramedullary orthopaedic surgical instrument" is a surgical tool configured to be positioned in the medullary canal of the patient's femur during the orthopaedic surgical procedure. Examples of intramedullary orthopaedic surgical instruments include femoral stem trials, femoral broaches, and the like. As shown in FIG. 1, the intramedullary orthopaedic surgical instrument 16 includes a stem trial 18, which may be used to size and select a prosthetic stem component.

The stem trial 18 includes an elongated body 20 that defines a longitudinal axis 22 extending through the distal end 24 and the proximal end 26. A plurality of external threads 28 are defined on the distal end 24 of the stem trial 18. As described in greater detail below, the external threads 28 are configured to engage a plurality of internal threads 30 (see FIG. 4) formed on the offset guide assembly 14 to secure the stem trial 18 to the assembly 14. In the illustrative embodiment, the stem trial 18 is formed from a metallic material, such as, for example, a stainless steel or a cobalt chromium alloy.

Figure 2:
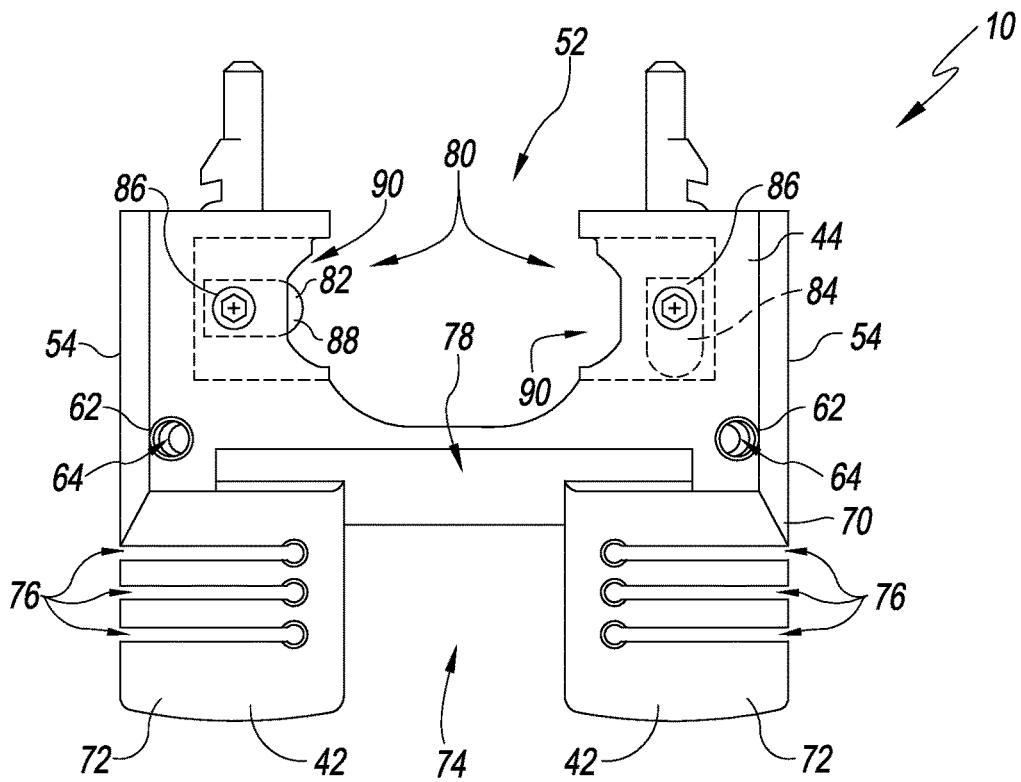
FIG. 2 is a plan view of the cutting block of FIG. 1.
Figure 3:
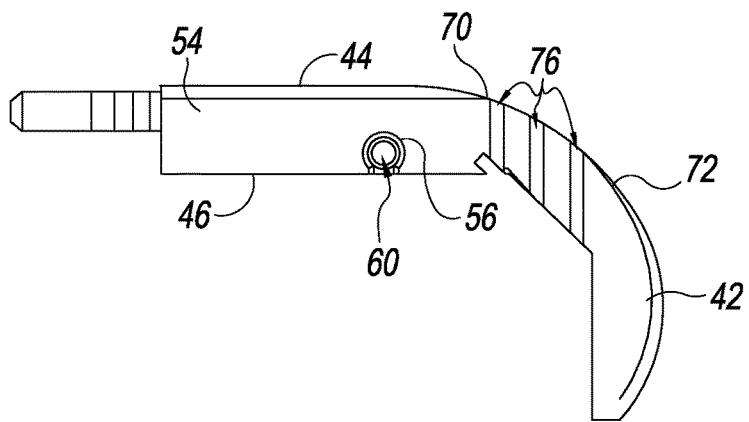
FIG. 3 is an elevation view of the cutting block of FIGS. 1-2.

As described above, the instrument system 10 includes a base cutting block 12 configured for use on a femur of a patient. As shown in FIGS. 1-3, the base cutting block 12 includes a base plate 40 and a pair of arms 42 extending from the base plate 40. It should be appreciated that in other embodiments the base cutting block 12 may have a different configuration including, for example, only the base plate 40. The base plate 40 and the arms 42 of the base cutting block 12 are formed from a metallic material, such as, for example, a stainless steel or a cobalt chromium alloy. The base plate 40 includes a distal surface 44 and a proximal surface 36 positioned opposite the distal surface 44. An opening 48 is defined in the distal surface 44, and an inner wall 50 extends distally through the base plate 40 to define a receiving slot 52.

As shown in FIGS. 2-3, the base plate 40 of the base cutting block 12 has a pair of side walls 54 that extend between the distal surface 44 and the proximal surface 46. Each side wall 54 has an opening 56 defined therein and a channel 60 extends inwardly from each opening 56. Each channel 60 is sized to receive a mounting shaft or pin from another surgical instrument such as, for example, a distal spacer block. It should be appreciated that in other embodiments the channels 60 may be omitted.

As shown in FIG. 2, the base cutting block 12 also includes a pair of fastener guides 62 that are defined in the base plate 40. Each fastener guide 62 includes a bore 64 that is sized to receive fasteners such as, for example, fixation pins, which may be utilized to secure the base cutting block 12 to the patient's femur. It should be appreciated that in other embodiments the base cutting block 12 may include additional fastener guides 62 or other fastening elements to secure the cutting block to the patient's femur. Each channel 60 of the block 12 is aligned with one of the fastener guides 62 such that the bore 64 of the fastener guide 62 opens into the channel 60.

As described above, the base cutting block 12 also includes a pair of arms 42 that extend posteriorly from a posterior side 70 of the base plate 40. Each arm 42 includes an articulating surface 72 shaped to match or correspond to a condylar surface of a femoral prosthetic component. In that way, the articulating surfaces 72 of the arms 42 are configured to contact a natural or prosthetic bearing surface of the patient's tibia. The arms 42 are spaced apart such that an opening 74 is defined therebetween.

The base cutting block 12 includes a number of cutting guides that may be used during an orthopaedic surgical procedure to resect a portion of a patient's femur. For example, as shown in FIG. 2, the base cutting block 12 includes a number of posterior cutting guides 76 defined in the arms 42 and a posterior chamfer cutting guide 78 defined in the base plate 40. Each cutting guide 76, 78 includes an elongated slot sized to receive a cutting saw blade of a surgical saw or other surgical device. In the illustrative embodiment, the posterior cutting guides 76 are positioned to guide the resection of the posterior surfaces 628 (see FIG. 24) of the distal end 622 of the patient's femur 620 when the base cutting block 12 is attached to the femur 620. The posterior chamfer cutting guide 78 is positioned to guide the resection of the posterior chamfer surfaces 630 of the distal end 622 of the patient's femur 620.

As described above, the system 10 also includes an offset guide assembly 14 that may be secured to the base cutting block 12. As shown in FIG. 2, the system 10 includes a locking mechanism 80 configured to secure the base cutting block 12 to the offset guide assembly 14. In the illustrative embodiment, the locking mechanism 80 includes a pair of locking tabs 82, 84 pivotally coupled to the base cutting block 12. Each of the locking tabs 82, 84 is coupled to the block 12 via a joint 86, which permits each of the locking tabs 82, 84 to pivot between a locked position (see tab 82) and an unlocked position (see tab 84). In the unlocked position, an ear 88 of the locking tab is positioned in an aperture 90 defined in the base plate 40 adjacent to the receiving slot 52 of the base cutting block 12. In the locked position, the ears 88 are positioned in the receiving slot 52 to thereby engage a mounting bracket 92 of a surgical instrument such as, for example, a guide block 100 of the offset guide assembly 14 when positioned in the slot 52, as described in greater detail below.

Figure 13:
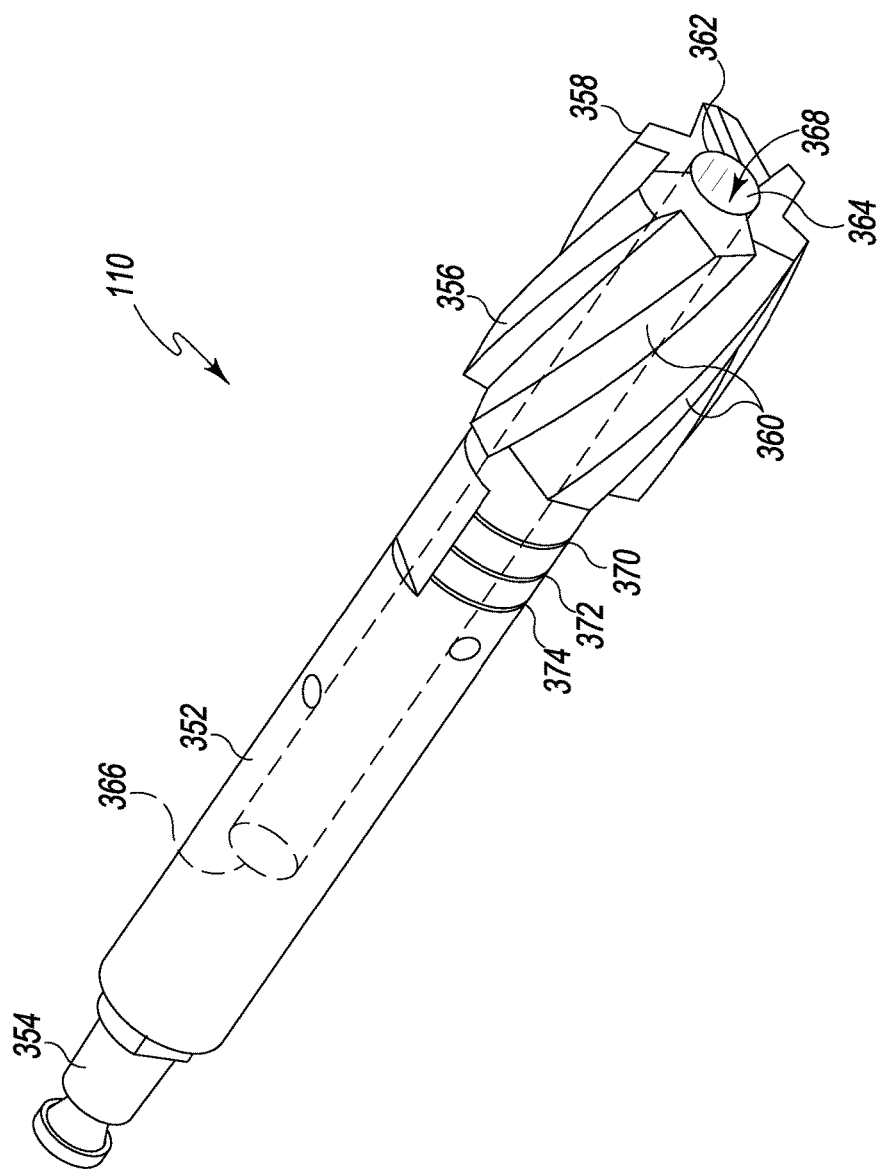
FIG. 13 is a perspective view of a surgical reamer of the orthopaedic surgical instrument system.

Returning to FIG. 1, the offset guide assembly 14 (hereinafter assembly 14) includes the guide block 100 that may be coupled to the base cutting block 12 and an offset guide tool 102 configured to be secured to the intramedullary orthopaedic surgical instrument 16. In the illustrative embodiment, the guide block 100 and the offset guide tool 102 are formed from metallic materials, such as, for example, stainless steel or cobalt chromium alloy. The guide block 100 includes a cylindrical passageway 104 sized to receive a guide shaft 106 of the offset guide tool 102. The assembly 14 also includes a locking mechanism 108 configured to secure the guide block 100 to the guide shaft 106, as described in greater detail below. In the illustrative embodiment, the guide block 100 and the offset guide tool 102 are used with the intramedullary orthopaedic surgical instrument 16 and the cutting block 12 to plan the reaming of the distal end 622 of the patient's femur 620. A surgical reamer 110, which is shown in FIG. 13 may be advanced over the guide shaft 106 to ream and otherwise cut the distal end 622 of the patient's femur 620.

Figure 4:
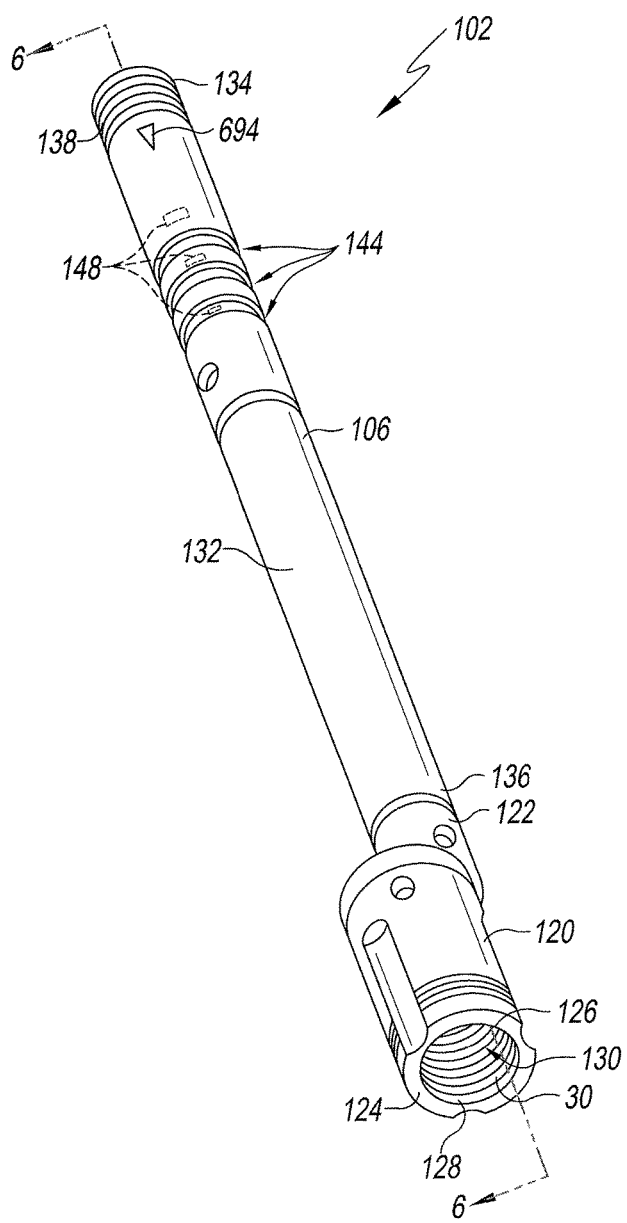
FIG. 4 is a perspective view of an offset guide tool of the offset guide assembly of FIG. 1.

Referring now to FIGS. 4-7, the offset guide tool 102 includes the guide shaft 106 and a mounting shaft 120 attached to the guide shaft 106 via a connecting body 122. As described in greater detail below, the guide shaft 106 may be pivoted relative to the mounting shaft 120. As shown in FIG. 4, the mounting shaft 120 of the tool 102 includes a proximal end 124 and an opening 126 defined in the proximal end 124. An inner wall 128 extends inwardly from the opening 126 to define a passageway 130 extending through the mounting shaft 120. A plurality of internal threads 30 are defined in the inner wall 128. As described above, the internal threads 30 are configured to engage the external threads 28 of the stem trial 18, thereby securing the stem trial 18 to the guide tool 102.

Figure 5:
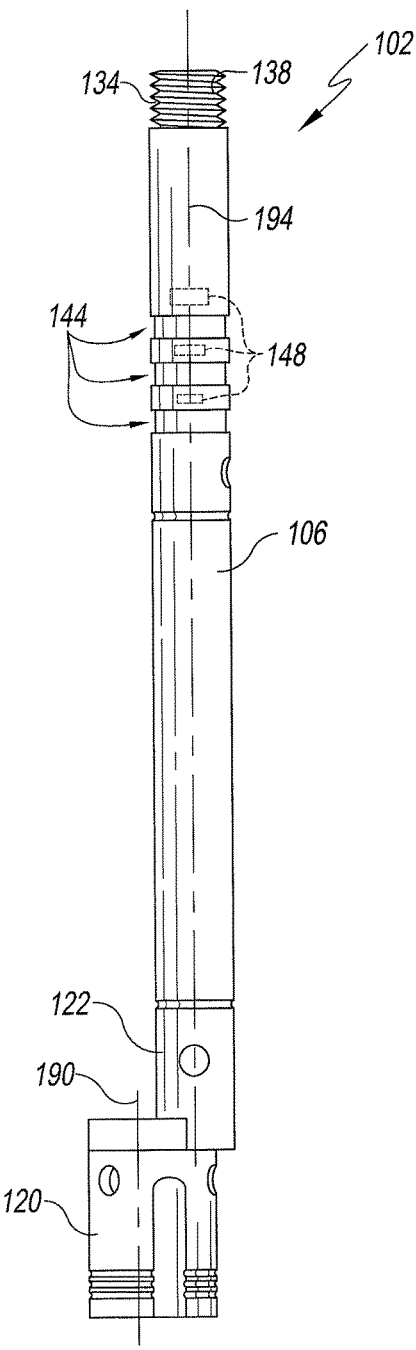
FIG. 5 is an elevation view of the offset guide tool of FIG. 4.

As shown in FIGS. 4-5, the guide shaft 106 includes a cylindrical body 132 extending from a distal end 134 to a proximal end 136. A plurality of external threads 138 are formed on the body 132 at the distal end 134. As described in greater detail below, the external threads 138 are configured to engage a plurality of internal threads 140 of a handle assembly 280 (see FIG. 12) that may be used to pivot or rotate the guide shaft 106 relative to the mounting shaft 120. A plurality of slots 144 are defined in the outer surface 146 of the cylindrical body 132. Each slot 144 defines a desired attachment location of the guide block 100. As described in greater detail below, each attachment location of guide block 100 corresponds to a number of different reaming depths. A plurality of markings 148 are defined on the outer surface 146, and each marking 148 is associated with one of the slots 144 to indicate the attachment location to the user.

As shown in FIG. 6, an opening 150 is defined in the distal end 134 of the cylindrical body 132, and an opening 152 is defined in the opposite proximal end 136 of the body 132. An inner wall 154 extends inwardly from the opening 152 to an annular surface 156. The annular surface 156 and the inner wall 154 cooperate to define a distal aperture 158 in the cylindrical body 132. Another inner wall 160 extends inwardly from the proximal opening 152 to define a passageway 162 that connects to the distal aperture 158.

The connecting body 122 of the guide tool 102 includes a distal post 170 that is positioned in the aperture 158 of the cylindrical body 132. The connecting body 122 is secured to the cylindrical body 132 via a fastener (not shown) such as a pin or tab. In other embodiments, the cylindrical body 132 and the connecting body 122 may be secured via a press fit, taper fit, welding, or other fastening process. In the illustrative embodiment, the post 170 (and hence the connecting body 122) is not permitted to rotate relative to the guide shaft 106.

The connecting body 122 of the guide tool 102 also includes a proximal surface 172 and a proximal post 174 extending from the proximal surface 172. As shown in FIG. 6, the proximal post 174 is offset from the distal post 170 and is received in the passageway 130 defined in the mounting shaft 120. The post 174 is coupled to the mounting shaft 120 via a joint 176 that permits relative movement between the mounting shaft 120 and the connecting body 122 (and hence the guide shaft 106). In the illustrative embodiment, the joint 176 includes a locking ring 178 that is received in annular slots 180 defined in the surfaces 182, 184 of the post 174 and the mounting shaft 120, respectively. In that way, the ring 178 retains the mounting shaft 120 on the post 174.

As shown in FIG. 6, the mounting shaft 120 has a longitudinal axis 190 extending through its ends 124, 192. The cylindrical body 132 has a longitudinal axis 194 extending through its ends 134, 136 that extends parallel to the longitudinal axis 190. In the illustrative embodiment, the axis 190 is offset from the axis 194 by approximately 4 millimeters, which matches the offset of the implant, as described in greater detail below. In other embodiments, the offset of the implant may greater than or less than 4 millimeters. As described above, the mounting shaft 120 is pivotally coupled to the guide shaft 106 via the connecting body 122. When the mounting shaft 120 is held fixed, the connecting body 122 and the guide shaft 106 may be rotated about the longitudinal axis 190. Conversely, the mounting shaft 120 may be rotated about the longitudinal axis 190 when the connecting body 122 or the guide shaft 106 is held fixed.

As shown in FIGS. 6-7, the guide tool 102 also includes a locking mechanism 200 configured to prevent relative rotation between the mounting shaft 120 and the connecting body 122 (and hence the guide shaft 106). In the illustrative embodiment, the locking mechanism 200 includes a rod 202 having a distal end 204 positioned in the passageway 162 of the guide shaft 106. As shown in FIG. 6, the connecting body 122 has a passageway 208 extending through the distal post 170, and the rod 202 extends into the passageway 208.

A plurality of internal threads 210 are defined on the inner wall of the connecting body 122, and a corresponding plurality of external threads 212 are formed on a proximal end 214 of the rod 202. The rod 202 has a tip 216 at the proximal end 214 that is received in a bore 218 defined in the connecting body 122. As shown in FIG. 6, the bore 218 has an opening 220 in the proximal surface 172, and an outer wall 222 of the mounting shaft 120 is aligned with that opening 220.

The rod 202 may be rotated relative to the guide shaft 106 and the connecting body 122 and thereby moved along the longitudinal axis 194 between an unlocked position (see FIG. 6) and a locked position (see FIG. 7). In the unlocked position, the tip 216 of the rod 202 is spaced apart from the outer wall 222 of the mounting shaft 120. When the rod 202 is rotated in the direction indicated by arrow 224 in FIG. 6, the tip 216 is advanced into contact with the outer wall 222 of the mounting shaft 120, thereby preventing relative movement between the mounting shaft 120 and the connecting body 122 (and hence the guide shaft 106).

Figure 8:
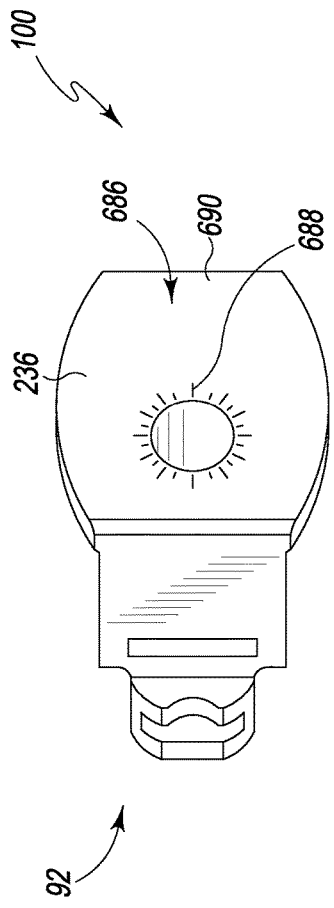
FIG. 8 is an perspective view of a guide block of the offset guide assembly of FIG. 1.
Figure 10:
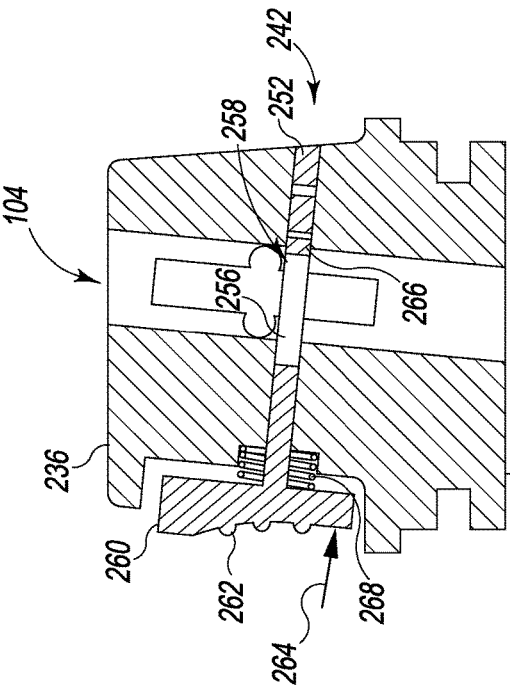
FIG. 10 is a cross-sectional elevation view of the guide block taken along the line 10-10 in FIG. 8.
Figure 9:
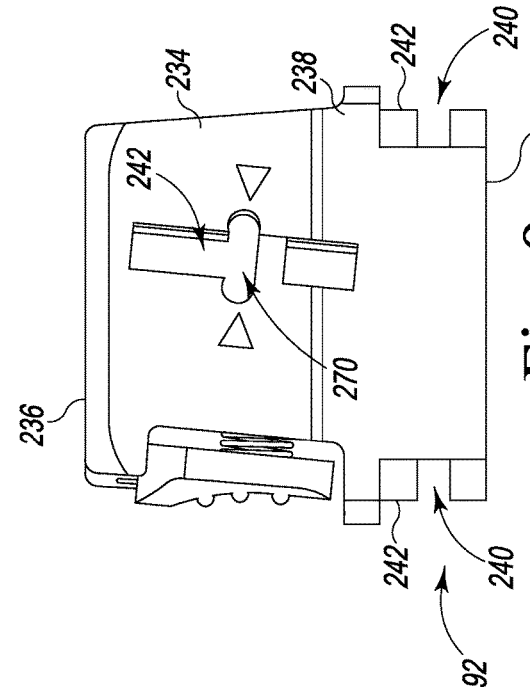
FIG. 9 is an elevation view of the guide block of FIG. 8.

As described above, the offset guide assembly 14 also includes a guide block 100 configured to be secured to the base cutting block 12. Referring now to FIGS. 8-10, the guide block 100 includes a mounting bracket 92 positioned at a proximal end 232 and a body 234 extending from the bracket 92 to a distal end 236. As described above, the mounting bracket 92 is configured to receive the locking tabs 82, 84 of the base cutting block 12. In the illustrative embodiment, the bracket 92 includes a base 238 sized to be positioned in the receiving slot 52 of the cutting block 12. As shown in FIG. 9, a channel 240 is defined in each side 242 of the base 238. Each channel 240 is sized to receive one of the ears 88 of the locking tabs 82, 84 when the tabs 82, 84 are in the locked position and the base 238 is positioned in the receiving slot 52. In that way, the guide block 100 may be secured to the cutting block 12.

As shown in FIG. 10, a cylindrical passageway 104 extends through the ends 232, 236 of the guide block 100. The cylindrical passageway 104 is sized receive the guide shaft 106 of guide tool 102. As shown in FIG. 9, the body 234 of the guide block 100 has an elongated slot 242 defined therein. The slot 242 connects to the passageway 104 and extends parallel to the passageway 104.

As described above, the guide block 100 includes a locking mechanism 108 configured to attach the block 100 to the guide shaft 106. In the illustrative embodiment, the locking mechanism 108 includes a pin or plate 252 positioned in a slot 254 defined in the body 234 of the block 100. As shown in FIG. 10, the slot 254 (and hence the plate 252) extends transverse to the passageway 104. The plate 252 includes an annular wall 256, which defines a bore 258 sized to receive the guide shaft 106.

The locking mechanism 108 also includes a user-operated button 260 that is attached to the plate 252. As shown in FIGS. 9-10, the user-operated button 260 includes a contoured surface 262, which may be pressed to move the plate 252 in the direction indicated by arrow 264 between a locked position and an unlocked position. In the locked position, a wall section 266 of the plate 252 is positioned in the passageway 104; in the unlocked position, the bore 258 defined in the plate 252 is coaxial with the passageway 104. In the illustrative embodiment, the locking mechanism 108 includes a biasing element such as, for example, a spring 268 positioned between the body 234 and the button 260 to bias the plate 252 in the locked position.

In use, the distal end 134 of the guide shaft 106 is positioned below the proximal end 232 of the guide block 100 and aligned with the passageway 104. The distal end 134 of the guide shaft 106 may be advanced into the passageway 104. The button 260 may be pressed to move the plate 252 to the unlocked position, thereby permitting the distal end 134 to advance through the bore 258 of the plate 252 and out of the passageway 104.

One of the slots 144 defined in the outer surface 146 of the guide shaft 106 may be aligned with the plate 252 to locate the guide block 100 in a desired position. As described above, each slot 144 has a marking 148 associated with it to indicate the attachment location. When each slot 144 is aligned with the plate 252, the marking 148 associated with that slot 144 is visible through a window 270 extending transverse to the elongated slot 242. When the button 260 is released, the spring 268 urges the plate 252 toward the locked position, thereby advancing the wall section 266 of the plate 252 into the selected slot 144. In that way, the guide block 100 may be secured to the guide tool 102. When the guide block 100 and the cutting block 12 are secured to guide shaft 106, an oblique angle is defined between the proximal surface 46 of the cutting block 12 and the axis 194 of the guide shaft 106. It should be appreciated that in other embodiments the guide shaft may include only a single slot or attachment location. In such embodiments, a number of different-sized guide blocks may be used to obtain the desired depth.

Figure 12:
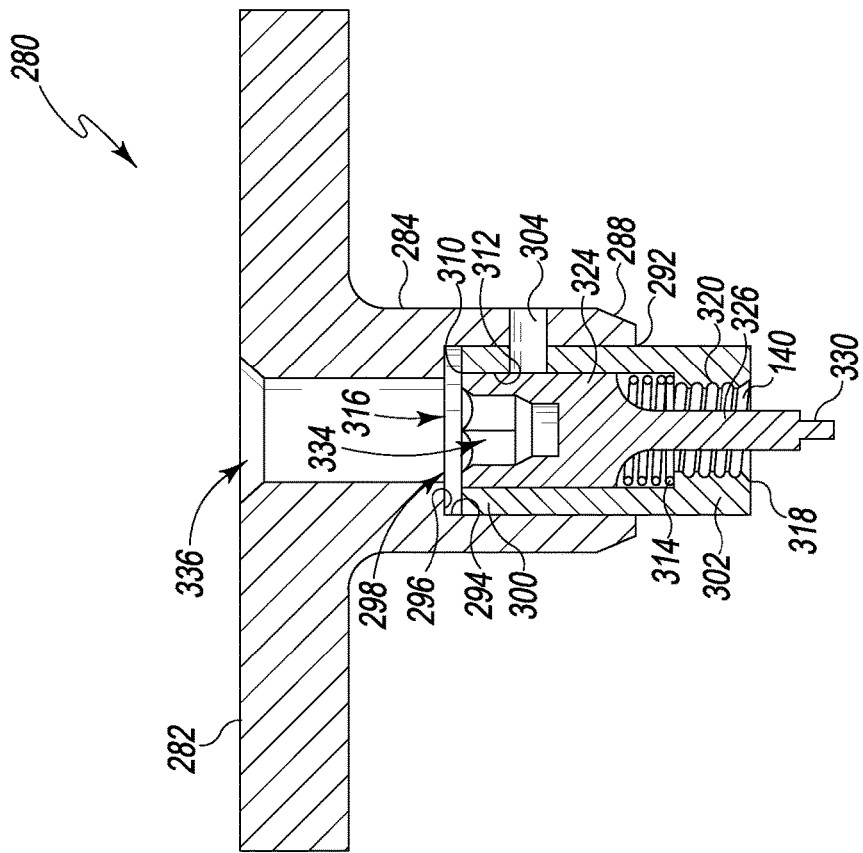
FIG. 12 is a cross-sectional elevation view of the handle assembly taken along the line 12-12 in FIG. 11.
Figure 11:
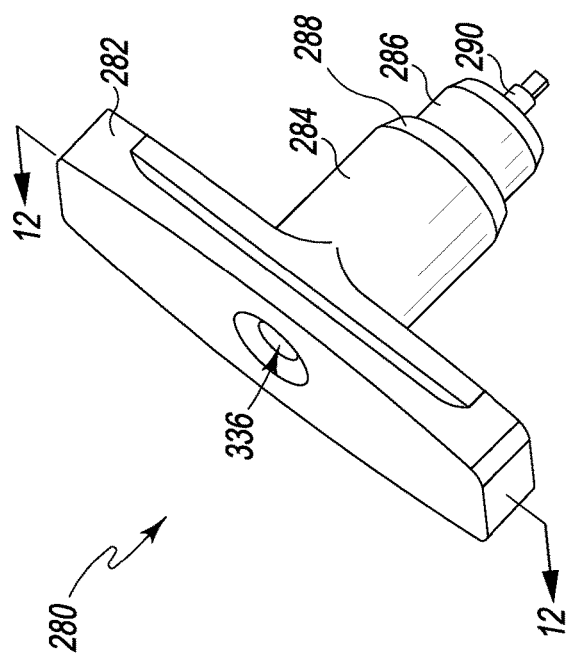
FIG. 11 is a perspective view of a handle assembly of the orthopaedic surgical instrument system.

Referring now to FIGS. 11-12, a handle assembly 280 of the offset guide assembly 14 is shown. The handle assembly 280 is operable to rotate the guide shaft 106 relative to the mounting shaft 120 when the mounting shaft 120 is held fixed, such as, for example, when the mounting shaft 120 is seated in the medullary canal of the patient's femur, as described in greater detail below. The handle assembly 280 includes an elongated grip 282 and a central housing 284 extending away from the grip 282. As shown in FIG. 11, the grip 282 and the housing 284 form the shape of a "T-handle." It should be appreciated that in other embodiments the handle assembly 280 may have a different configuration. The handle assembly 280 also includes a mounting tube 286 extending from the proximal end 288 of the housing 284 and a connecting shaft 290 pivotally coupled to the mounting tube 286.

As shown in FIG. 12, the housing 284 has an opening 292 in the proximal end 288, and an inner wall 294 extends inwardly from the opening 292 to an annular surface 296. The inner wall 294 and the annular surface 296 cooperate to define an aperture 298 in the housing 284. The mounting tube 286 of the handle assembly 280 extends from a distal end 300 positioned in the aperture 298 to a proximal end 302. In the illustrative embodiment, the mounting tube 286 is secured to the housing 284 via a cylindrical pin 304 such that relative movement between the mounting tube 286 and the housing 284 is prevented. The handle assembly 280 may be formed from a metallic material such as stainless steel, cobalt chrome, or titanium, although other metals or alloys may be used. Moreover, in some embodiments, rigid polymers such as polyetheretherketone (PEEK) may also be used.

The mounting tube 286 has an opening 310 defined in the distal end 300, and an inner wall 312 extends inwardly therefrom to an annular surface 314. The annular surface 314 cooperates with the wall 312 to define a distal passageway 316. The mounting tube 286 has another opening 318 defined in the proximal end 302, and an inner wall 320 extends inwardly therefrom to define a proximal passageway 322. As shown in FIG. 12, internal threads 140 are formed on the inner wall 320 adjacent to the proximal end 302. As described above, the internal threads 140 engage the external threads 138 formed on the distal end 134 of the guide shaft 106 to secure the handle assembly 280 to the offset guide tool 102.

As shown in FIG. 12, the connecting shaft 290 of the handle assembly 280 extends through the passageways 316, 322. The connecting shaft 290 includes a plug 324 and an elongated body 326 extending from the plug 324. The elongated body 326 extends away from the plug 324 to a tip 330. The tip 330 is configured to engage the rod 202 of the locking mechanism 200 such that the rod 202 may be moved between the locked and unlocked positions. In the illustrative embodiment, the tip 330 is formed as a hex-head. As shown in FIG. 7, a corresponding socket 332 is defined the distal end 204 of the rod 202.

Returning to FIG. 12, the plug 324 of the connecting shaft 290 has a socket 334 defined therein. The socket 334 is sized to receive a driver head 702 of a surgical instrument 700, which may be used to rotate the connecting shaft 290. The handle assembly 280 has a passageway 336 that extends through the elongated grip 282 and is connected to the aperture 298 defined in the housing 284. The passageway 336 is sized to permit the passage of the driver head 702.

The handle assembly 280 also includes a biasing element such as, for example, helical spring 338 to bias the plug 324 into engagement with the annular surface 296 of the housing 284. In the illustrative embodiment, the spring 338 is positioned between the plug 324 and the annular surface 314 of the mounting tube 286.

In use, the plug 324 of the connecting shaft 290 is initially positioned at the distal end 300 of the mounting tube 286 and engaged with the housing 284. When the housing assembly 280 is secured to the distal end 134 of the guide shaft 106, the driver head 702 may be advanced into the passageway 336 and positioned in the socket 334 of the connecting shaft 290. The plug 324 may be advanced along the distal passageway 316 of the mounting tube 286 to advance the tip 330 into the socket 332 of the rod 202. The connecting shaft 290 may then be rotated to move the rod 202 from the unlocked position to the locked position or from the locked position to the unlocked position. When the rod 202 is moved to the desired position, the driver head 702 may be withdrawn from the connecting shaft 290. The spring 338 then urges the connecting shaft 290 away from the rod 202.

Referring now to FIG. 13, the system 10 also includes a surgical reamer 110. In the illustrative embodiment, the reamer 110 is a cannulated reamer that is configured to be positioned on the guide shaft 106 to ream a portion of the patient's intramedullary canal. The reamer 110 includes an elongated body 352 including a shank 354 that fits into the chuck of a rotary power tool or a manual handle. In the illustrative embodiment, the shank 354 is a Hudson end. It should be appreciated that in other embodiments the shank may be configured to be received in a chuck. The reamer 110 also includes a cutting head 356 located at the opposite, proximal end 358 of the body 352. The cutting head 356 includes a plurality of helical cutting flutes 360. When the reamer 110 is engaged with the patient's femur and rotated, the cutting head 356 reams or otherwise cuts the bone tissue of the femur.

The reamer 110 has an opening 362 defined in the proximal end 358 of the elongated body 352. A cylindrical inner wall 364 extends inwardly from the opening 362 to an inner surface 366. The cylindrical inner wall 364 and the inner surface 366 cooperate to define an aperture 368 sized to receive the distal end 134 of the guide shaft 106. In that way, the guide shaft 106 may be used to guide the reamer 110 to ream or otherwise cut the bone tissue of the femur.

The reamer 110 may be constructed from a metallic material such as stainless steel, cobalt chrome, or titanium, although other metals or alloys may be used. Moreover, in some embodiments, rigid polymers such as polyetheretherketone (PEEK) may also be used.

The reamer 110 includes a number of depth marks 370, 372, 374 formed on its elongated body 352 at a location above the cutting head 356. Each of the depth marks 370, 372, 374 corresponds to a predetermined reaming depth that is required to implant the revision femoral prosthesis 650. During a surgical procedure, the reamer 110 is advanced over the guide shaft 106 deeper into the intramedullary canal of the patient's femur until the desired depth mark aligns with the distal surface of the patient's femur. In such a way, over-reaming of the distal end of the canal is avoided if the reamer 110 is not driven beyond the appropriate depth mark.

Figure 14:
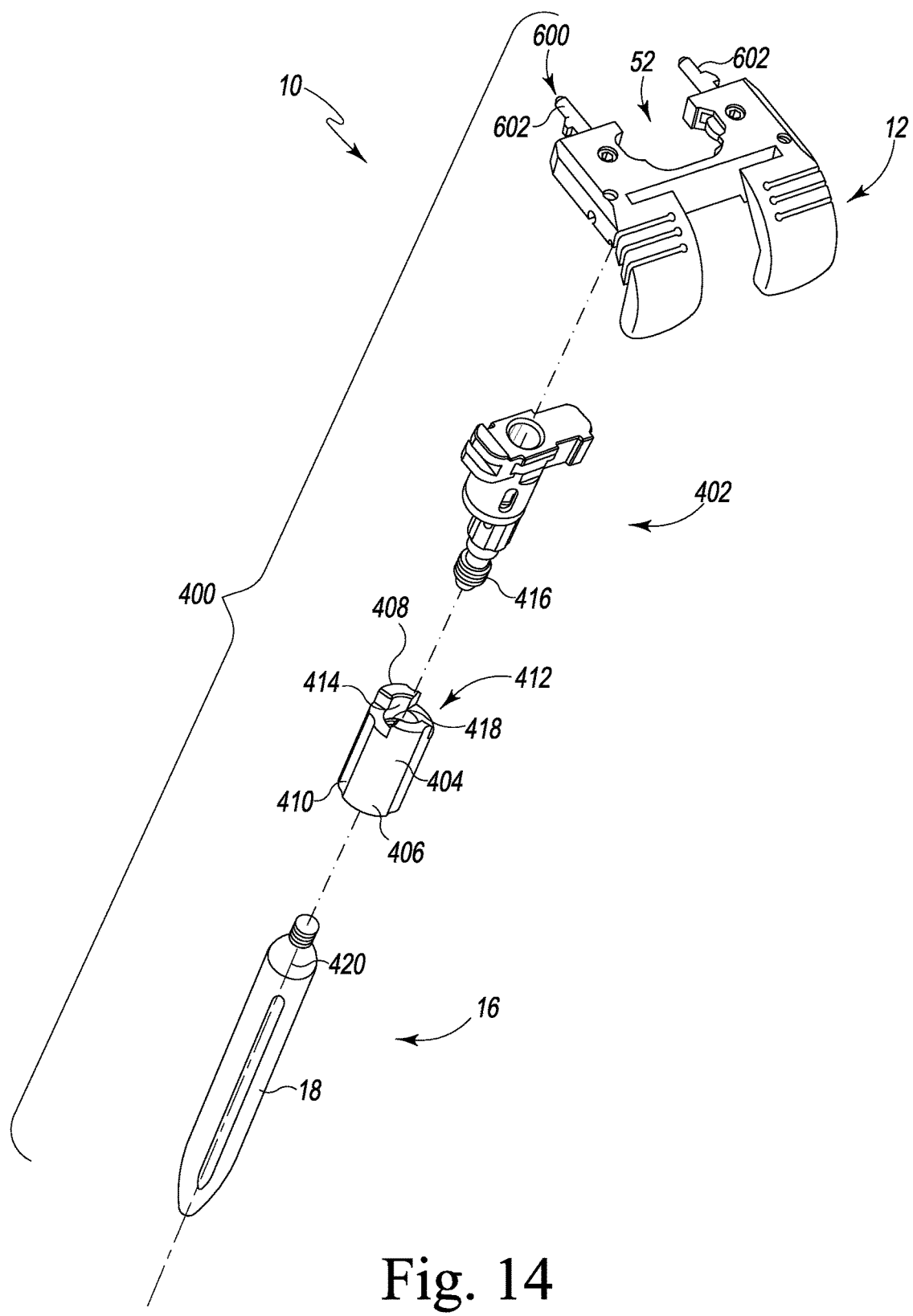
FIG. 14 is an exploded perspective view of an orthopaedic surgical instrument construct of the orthopaedic surgical instrument system.

Referring now to FIG. 14, an orthopaedic surgical instrument construct 400 of the system 10 is shown. The construct 400 includes the base cutting block 12, the intramedullary orthopaedic surgical instrument 16, and an intramedullary adaptor 402 configured to be coupled to the base cutting block 12 and the intramedullary orthopaedic surgical instrument 16. As shown in FIG. 14, the intramedullary orthopaedic surgical instrument 16 includes the stem trial 18 and a stem stabilizer 404 having a proximal end 406 secured to the stem trial 18 and a distal end 408 configured to be secured to the adaptor 402.

The stem stabilizer 404 is formed from a metallic material, such as, for example, a stainless steel or a cobalt chromium alloy. In other embodiments, the stabilizer 404 may be formed from a rigid polymer such as, for example polyetheretherketone (PEEK) may also be used. The stabilizer 404 includes a cylindrical body 410 having a central passageway 412 defined therein. In the illustrative embodiment, the cylindrical body 410 is devoid of any fins or projections. It should be appreciated that in other embodiments the stem stabilizer may include fins or projections to provide additional stability within the medullary canal.

Figure 15:
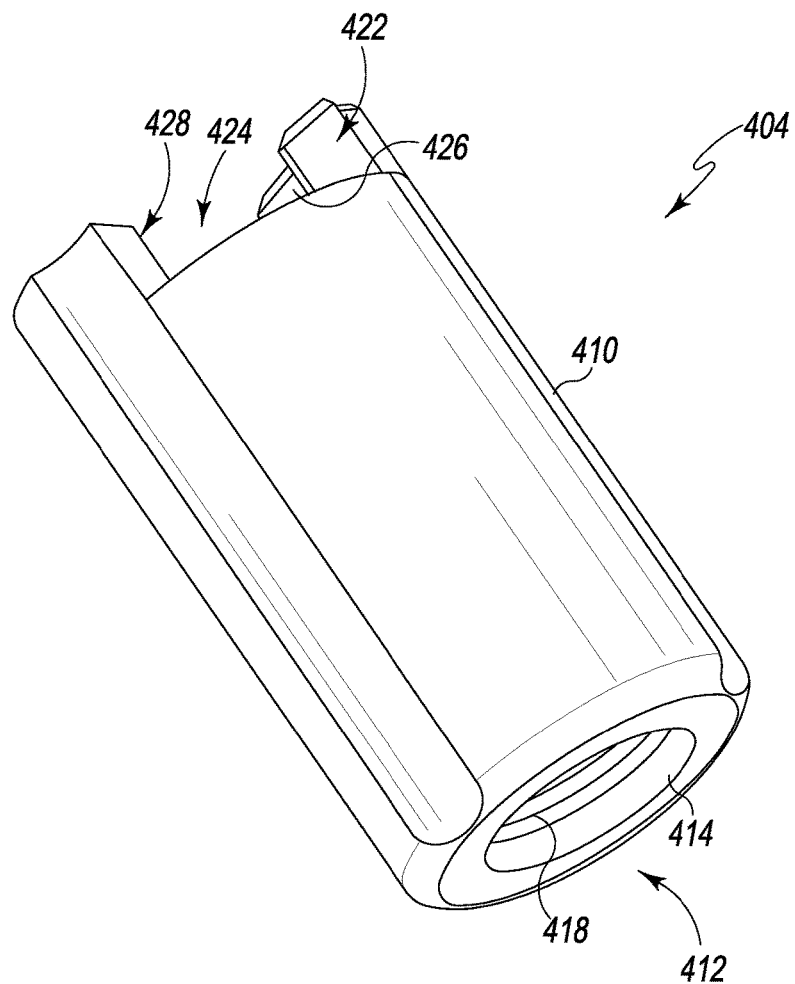
FIG. 15 is a perspective view of a stem stabilizer of the instrument construct of FIG. 14.

As shown in FIG. 15, a cylindrical inner wall 414 defines the passageway 412. A plurality of internal threads 418 are formed on the inner wall 414, which are configured to engage a plurality of external threads 416 formed on the adaptor 402. As such, the stabilizer 404 may be threaded onto the adaptor 402 to secure the stem stabilizer 404 to the adaptor 402. The internal threads 418 of the stem stabilizer 404 also correspond to the external threads 28 formed on the stem trial 18 such that the stem trial 18 may be threaded onto the stem stabilizer 404 to assemble the intramedullary surgical instrument 16. When the intramedullary surgical instrument 16 is assembled as shown in FIG. 14, the stem trial 18 and the stem stabilizer 404 cooperate to define a longitudinal axis 420 of the intramedullary surgical instrument 16.

The stem stabilizer 404 also includes a pair of channels 422, 424 defined in the distal end 408. The channel 422, 424 extends from the outer surface of the stabilizer 404 to the passageway 412. The inner wall 414 includes a pair of arced sections 426, 428 of the inner wall 414 that extend between the channels 422, 424. The arced sections 426, 428 are substantially smooth.

As described above, the construct 400 includes an intramedullary adaptor 402 configured to be secured to the base cutting block 12. What is meant herein by the term "intramedullary adaptor" is a surgical tool configured to be secured to an intramedullary orthopaedic surgical instrument and including an end sized and shaped to be positioned in a medullary canal of a patient's femur during the orthopaedic surgical procedure. As shown in FIGS. 16-17, the intramedullary adaptor 402 includes a mounting bracket 440 and a proximal adaptor body 442. An intermediate adaptor body 444 is pivotally coupled to the proximal adaptor body 442 and the mounting bracket 440, as described in greater detail below. Similar to the mounting bracket 92 of the guide block 100, the mounting bracket 440 is configured to receive the locking tabs 82, 84 of the base cutting block 12. In the illustrative embodiment, the bracket 440 includes a base 446 sized to be positioned in the receiving slot 52 of the cutting block 12. As shown in FIG. 16, the base 446 includes a pair of arms and a channel 240 is defined in each arm. Each channel 240 is sized to receive one of the ears 88 of the locking tabs 82, 84 when the tabs 82, 84 are in the locked position and the base 446 is positioned in the receiving slot 52. In that way, the intramedullary adaptor 402 may be secured to the cutting block 12.

As shown in FIG. 16, the mounting bracket 440 includes a central housing 448 that extends proximally from the base 446. The central housing 448 and the intermediate adaptor body 444 cooperate to define a longitudinal axis 450 of the intramedullary adaptor 402, as shown in FIG. 17. Another longitudinal axis 452 that extends parallel to the axis 450 is defined by the proximal adaptor body 442. In the illustrative embodiment, the axis 452 is offset from the axis 450 by 4 millimeters, which matches the offset of the implant, as described in greater detail below. In other words, the axes 450, 452 of the adaptor 402 are offset by the same distance as the axes 190, 194 of the offset guide tool 102.

As shown in FIG. 17, the mounting bracket 440 of the adaptor 402 has substantially planar distal surfaces 454, 456. The surfaces 454, 456 cooperate to define an imaginary plane 458 that extends transverse to the longitudinal axis 450. In the illustrative embodiment, an oblique angle 460 is defined between the axis 450 and the imaginary plane 458. In the illustrative embodiment, an oblique angle 460 is defined between the axis 450 and the imaginary plane 458, and the magnitude of the angle 460 matches the angle of the implant.

The proximal adaptor body 442 of the adaptor 402 has a distal end 470 coupled to the intermediate adaptor body 444 and a proximal end 472 configured to be secured to the orthopaedic intramedullary surgical instrument 16. As shown in FIG. 16, the proximal end 472 of the proximal adaptor body 442 includes a plurality of external threads 416 that engage the internal threads 418 of the stem stabilizer 404. The proximal adaptor body 442 has a contoured outer surface 474 adjacent to the distal end 470 and a passageway 476 that extends inwardly from an opening 478 defined in the proximal end 472.

Figure 18:
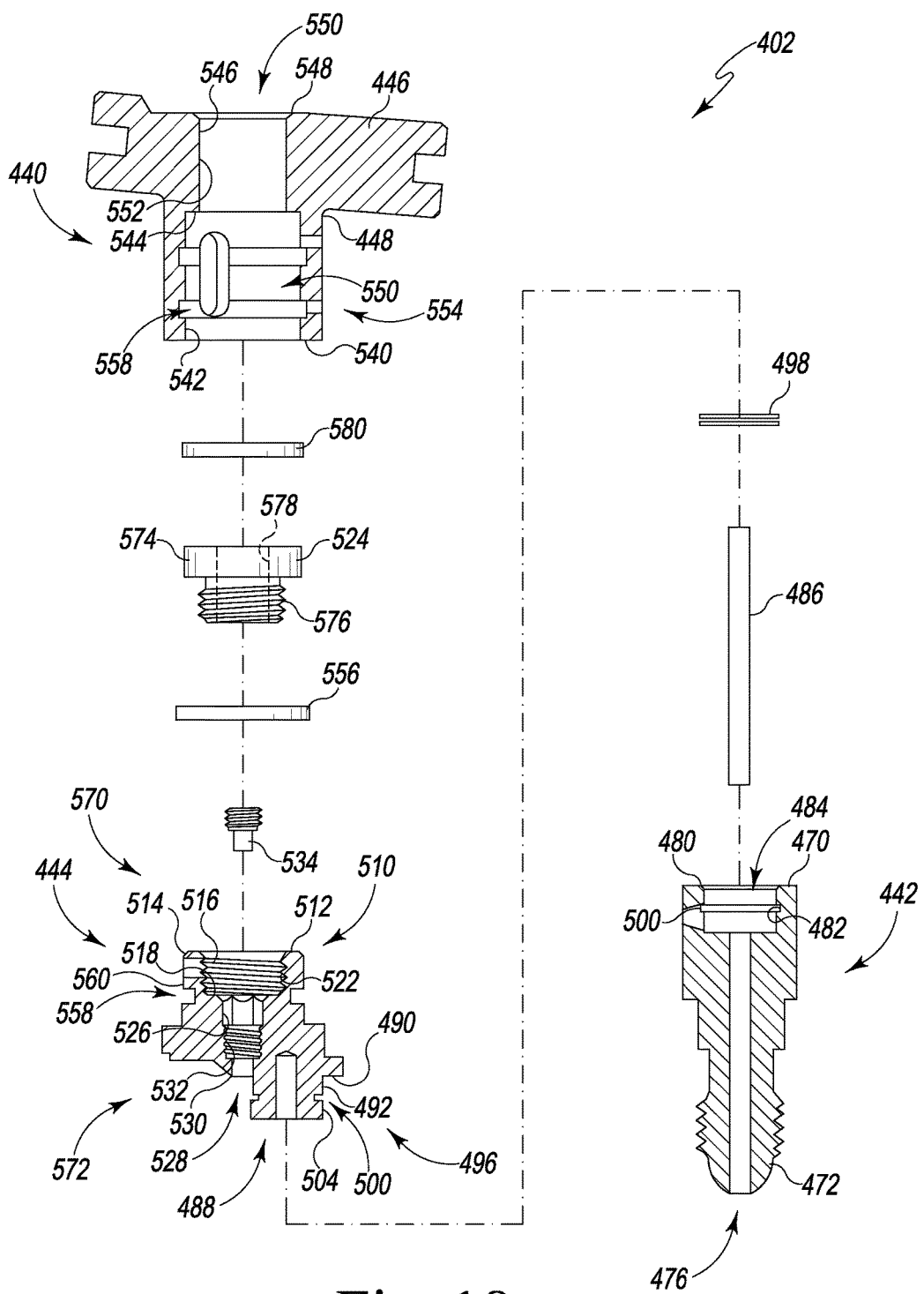
FIG. 18 is an exploded elevation view of the intramedullary adaptor of FIGS. 16-17.

As shown in FIG. 18, an opening 480 is defined in the opposite distal end 470 of the adaptor body 442. An inner wall 482 extends inwardly from the opening 480 to define a distal aperture 484 in the adaptor body 442. The proximal passageway 476 opens into the distal aperture 484 and, as shown in FIG. 18, is sized to receive a cylindrical rod 486.

The rod 486 extends into an aperture 488 defined in the intermediate adaptor body 444, as described in greater detail below.

The intermediate adaptor body 444 of the adaptor 402 includes a proximal surface 490 and a proximal post 492 extending from the proximal surface 490. As shown in FIG. 18, the aperture 488 is defined in the proximal post 492, and the proximal post 492 is configured to be received in the distal aperture 484 defined in the proximal adaptor body 442. In the illustrative embodiment, the post 492 is coupled to the adaptor body 442 via a joint 496 that permits relative movement between the adaptor bodies 442, 444. In the illustrative embodiment, the joint 496 includes a locking ring 498 that is received in annular slots 500 defined in the walls 482, 504 of the post 492 and the adaptor body 442, respectively. In that way, the ring 498 retains the adaptor body 442 on the post 492.

The intermediate adaptor body 444 of the adaptor 402 also includes a distal post 510 that is offset from the proximal post 492. As shown in FIG. 18, the distal post 510 has an opening 512 defined its end 514, and an inner wall 516 extends inwardly from the opening 512 to an annular surface 518. The wall 516 and the surface 518 cooperate to define a distal aperture 520 in the distal post 510. In the illustrative embodiment, internal threads 522 are formed on the inner wall 516. The internal threads 522 are configured to engage an externally-threaded insert 524, as described in greater detail below.

An inner wall 526 extends inwardly from the annular surface 518 to define a bore 528 in the adaptor body 444. As shown in FIG. 18, the bore 528 has an opening 530 defined in the proximal surface 490 of the body 444. In the illustrative embodiment, internal threads 532 are formed on the inner wall 526. The internal threads 532 are configured to engage an externally-threaded pin 534, as described in greater detail below.

As shown in FIG. 18, the mounting bracket 440 has an opening 540 defined in the central housing 448. An inner wall 542 extends inwardly from the opening 540 to an annular surface 544, and another inner wall 546 extends from the annular surface 544 to an opening 548 defined in the base 446 of the mounting bracket 440. The inner walls 542, 546 and the annular surface 544 cooperate to define a passageway 550 extending through the mounting bracket 440.

The proximal section 552 of the passageway 550 is sized to receive the distal post 510 of the adaptor body 444. In the illustrative embodiment, the post 510 is coupled to the mounting bracket 440 via a joint 554 that permits relative movement between the mounting bracket 440 and the adaptor body 444 (and hence the adaptor body 442). In the illustrative embodiment, the joint 554 includes a locking ring 556 that is received in annular slots 558 defined in the walls 542, 560 of the mounting bracket 440 and the post 510, respectively. In that way, the ring 556 retains the mounting bracket 440 on the post 510.

As described above, the intermediate adaptor body 444 of the adaptor 402 is pivotally coupled to the proximal adaptor body 442 and the mounting bracket 440 via joints 496, 554. As such, when the proximal adaptor body 442 is held fixed, the intermediate adaptor body 444 (and hence the mounting bracket 440) may be rotated about the longitudinal axis 452. Conversely, the proximal adaptor body 442 may be rotated about the axis 452 when the intermediate adaptor body 444 is held fixed. Additionally, when the mounting bracket 440 is held fixed, the intermediate adaptor body 444 (and hence the proximal adaptor body 442) may be rotated about the longitudinal axis 450. Conversely, the mounting bracket 440 may be rotated about the axis 452 when the intermediate adaptor body 444 is held fixed.

In the illustrative embodiment, the adaptor 402 includes a distal locking mechanism 570 configured to prevent relative movement between the intermediate adaptor body 444 and the mounting bracket 440. The adaptor 402 also includes a proximal locking mechanism 572 configured to prevent relative movement between the intermediate adaptor body 444 and the proximal adaptor body 442. As shown in FIG. 18, the distal locking mechanism 570 includes the threaded insert 524, which has a head 574 and a threaded shaft 576 extending from the head 574. A passageway 578 extends through the head 574 and the shaft 576—that is, the passageway 578 extends through the length of the threaded insert 524.

Figure 19:
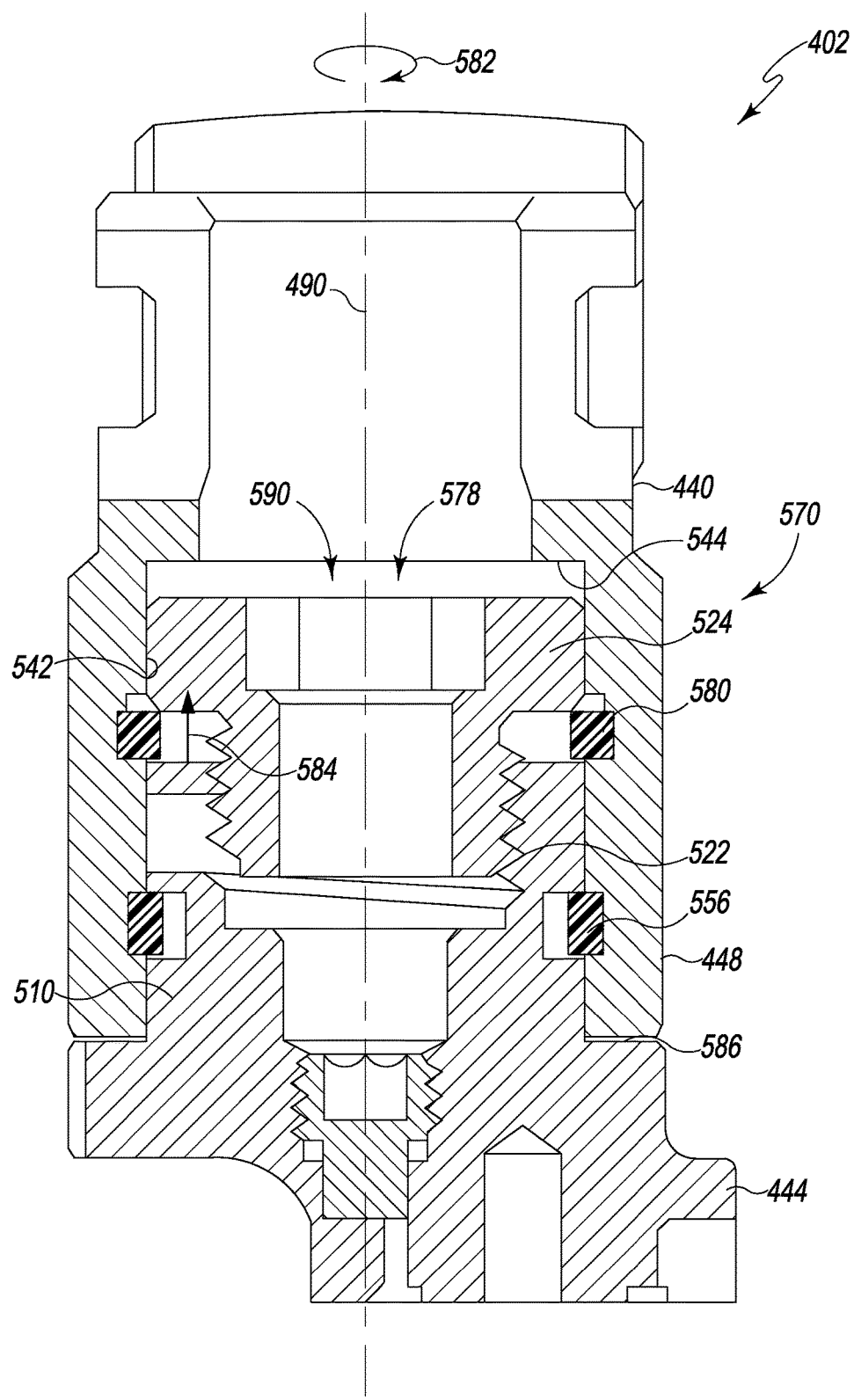
FIG. 19 is a fragmentary, cross-sectional elevation view taken along the line 19-19 in FIG. 17 showing a distal locking mechanism of the intramedullary adaptor in an unlocked position.

As shown in FIG. 19, the head 574 of the insert 524 is positioned between the annular surface 544 of the mounting bracket 440 and a locking ring 580 secured to the inner wall 542 of the mounting bracket 440. The threaded shaft 576 of the insert 524 engages the internal threads 522 of the distal post 510 of the adaptor body 444. In the illustrative embodiment, rotation of the insert 524 about the axis 490 causes the intermediate adaptor body 444 to move between an unlocked position (see FIG. 19) and a locked position (see FIG. 20).

Figure 20:
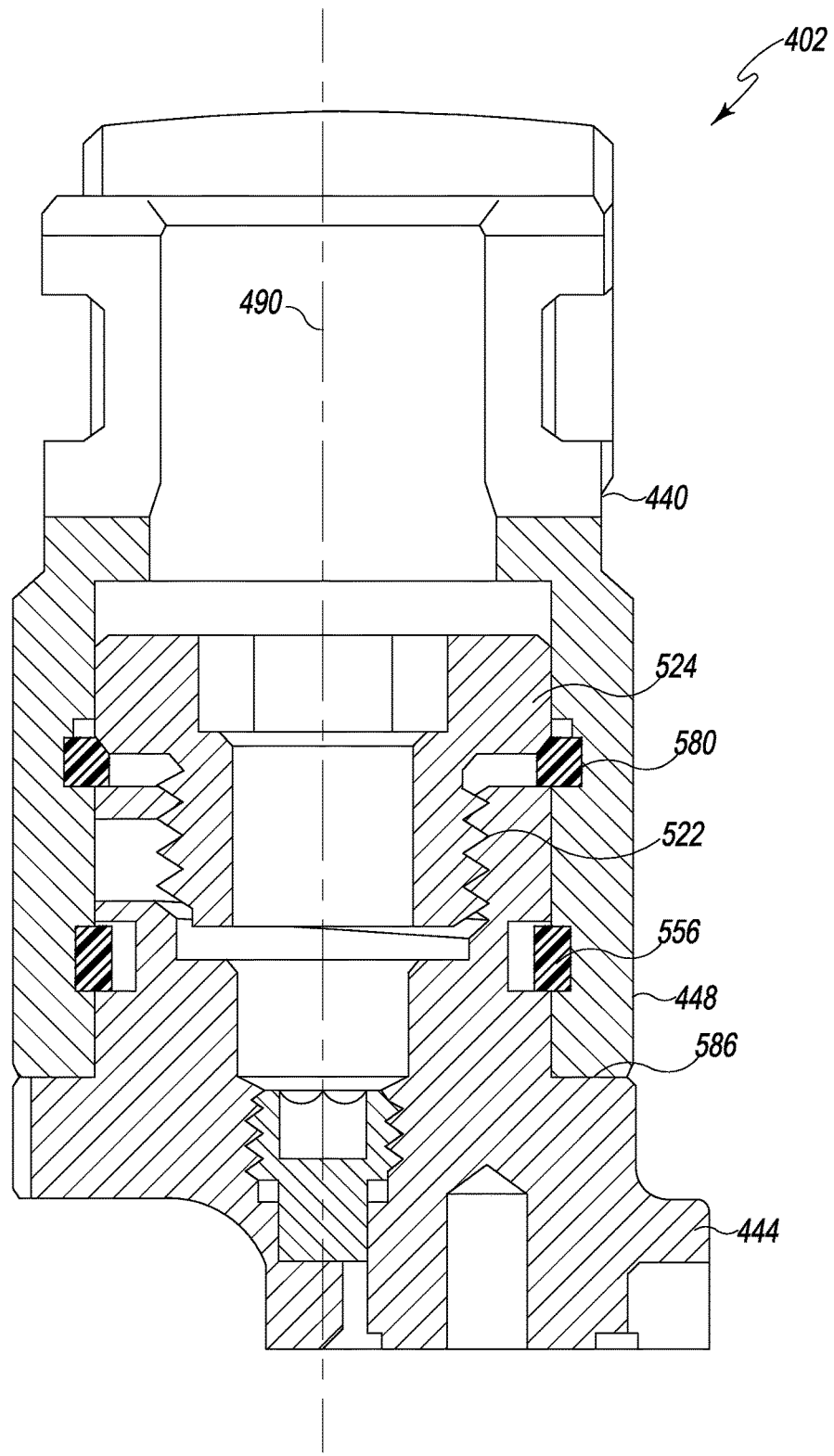
FIG. 20 is a view similar to FIG. 19 showing the distal locking mechanism of the intramedullary adaptor in a locked position.

In the unlocked position shown in FIG. 19, relative movement between the adaptor body 444 and the mounting bracket 440 is permitted. When the insert 524 is rotated about the axis 490 in the direction indicated by arrow 582 in FIG. 19, the insert 524 engages the locking ring 580, which prevents the insert 524 from moving proximally such that the distal post 510 of the adaptor body 444 is drawn distally along the axis 490, as indicated by arrow 584. As the distal post 510 is advanced along the axis 490, the distal post 510 engages the locking ring 580 and an annular flange 586 of the adaptor body 444 engages the central housing 448, as shown in FIG. 20. The engagement between the annular flange 586 of the body 444 and the central housing 448 prevents movement between the adaptor body 444 and the mounting bracket 440. The engagement between the post 510 and the locking ring 580 also assists in preventing movement between the adaptor body 444 and the mounting bracket 440.

As shown in FIGS. 19-20, the head 574 of the insert 524 has a socket 590 defined therein. The socket 590 is sized to receive a driver head 702 of a surgical instrument 700. When the driver head 702 is received in the socket 590, the instrument 700 may be used to rotate the insert 524 and thereby operate the locking mechanism 570.

Figure 21:
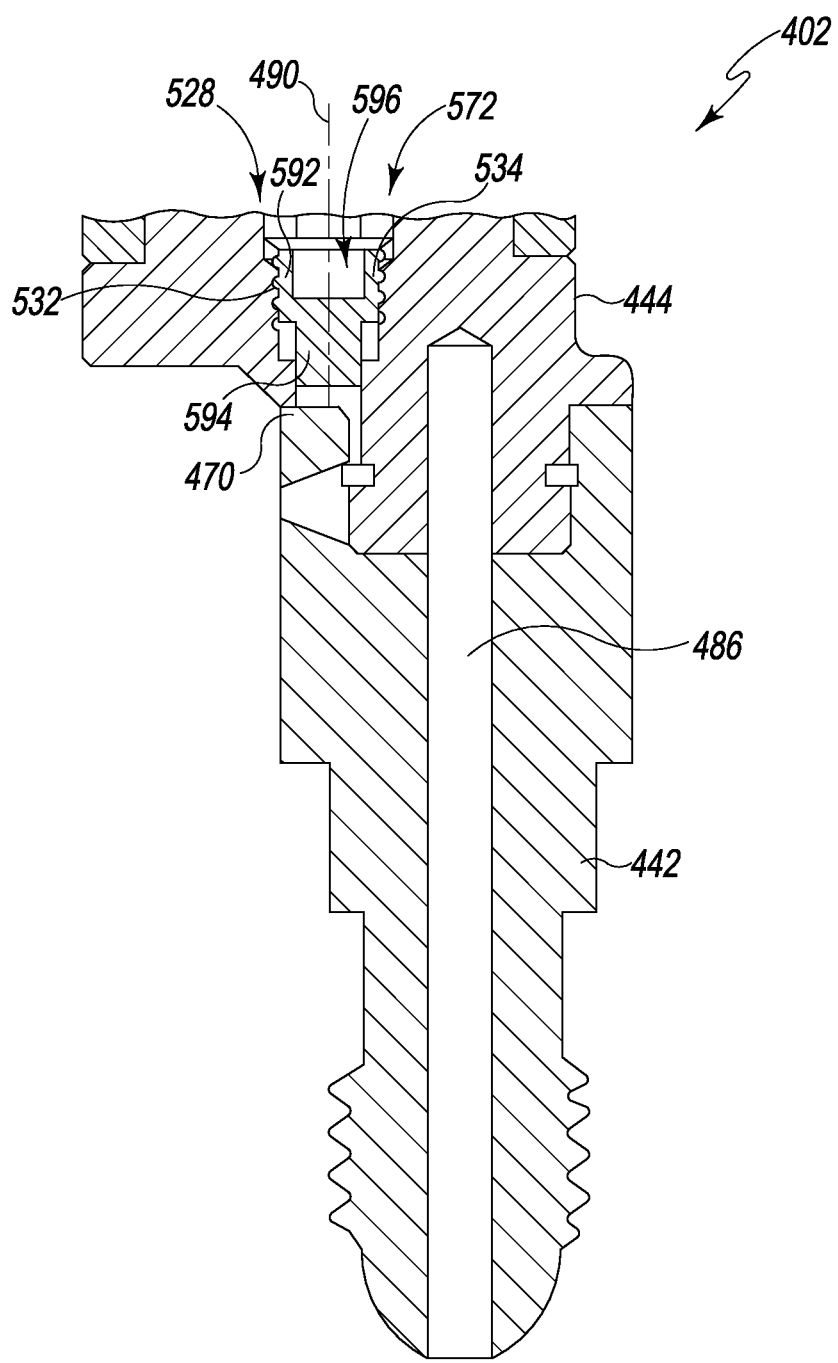
FIG. 21 is a fragmentary, cross-sectional elevation view taken along the line 19-19 in FIG. 17 showing a proximal locking mechanism of the intramedullary adaptor in an unlocked position.
Figure 22:
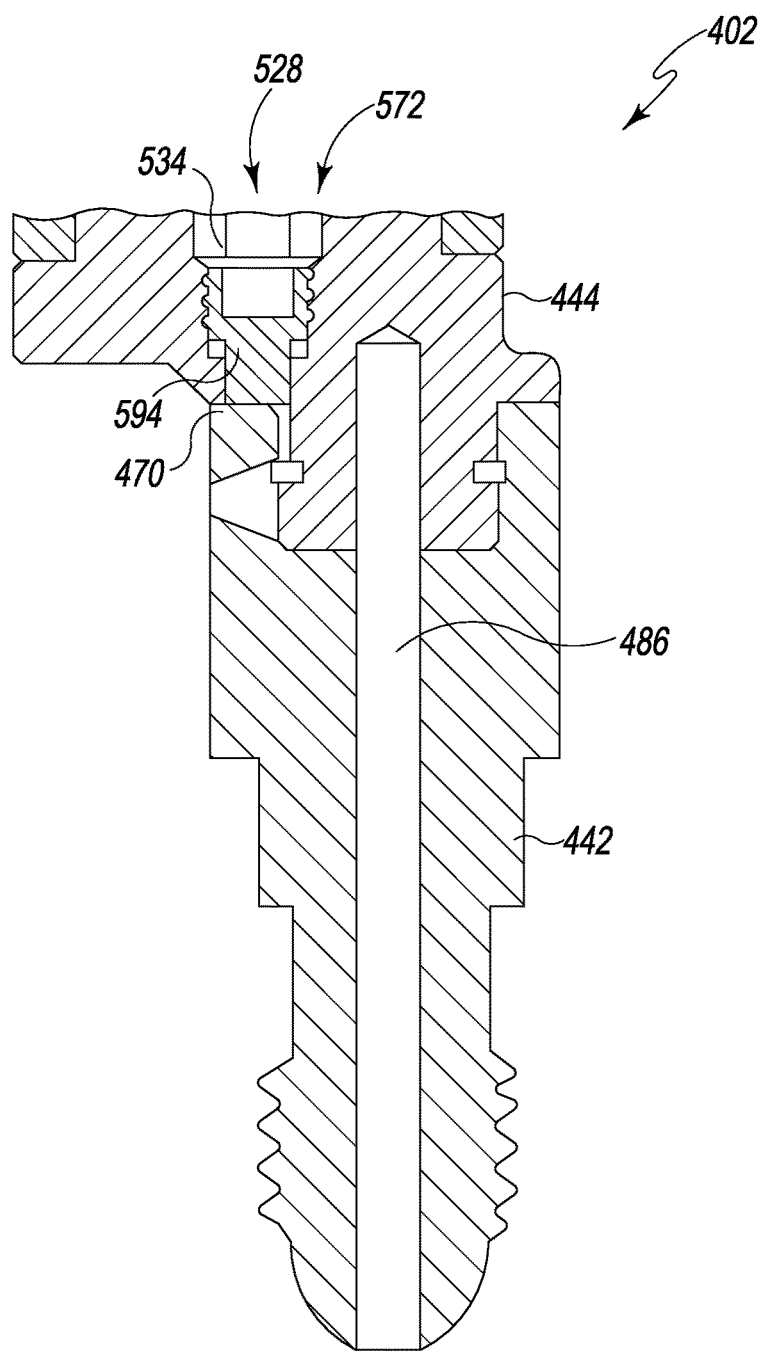
FIG. 22 is a view similar to FIG. 21 showing the proximal locking mechanism of the intramedullary adaptor in a locked position.

As described above, the adaptor 402 also includes a proximal locking mechanism 572 configured to prevent relative movement between the intermediate adaptor body 444 and the proximal adaptor body 442. As shown in FIGS. 21-22, the locking mechanism 572 includes the threaded pin 534. The pin 534 has a threaded plug 592 and an elongated shaft 594 extending from the plug 592. The threaded plug 592 of the pin 534 engages the internal threads 532 of the adaptor body 444. In the illustrative embodiment, rotation of the pin 534 about the axis 490 causes the pin 534 to move between an unlocked position (see FIG. 21) and a locked position (see FIG. 22). The pin 534 includes a socket 596 configured to receive a driver head (not shown), which may be advanced through the passageway 578 of the threaded insert 524.

In the unlocked position, the elongated shaft 594 of the pin 534 is positioned in the bore 528 of the adaptor body 444 and is spaced apart from the distal end 470 of the proximal adaptor body 442 such that relative movement between the intermediate adaptor body 444 and the proximal adaptor body 442 is permitted. When the pin 534 is rotated, the elongated shaft 594 is advanced proximally along the bore 528 and into engagement with the distal end 470 of the proximal adaptor body 442. The engagement between the pin 534 and the proximal adaptor body 442 prevents movement between the adaptor bodies 442, 444.

Returning to FIG. 14, the base cutting block 12 is configured to be coupled to a plurality of modular cutting blocks. A number of modular cutting blocks suitable for use with the base cutting block 12 are shown and described in U.S. patent application Ser. No. 13/485,470 entitled "FEMORAL ORTHOPAEDIC SURGICAL INSTRUMENTS AND METHOD OF USE OF SAME," which is incorporated herein by reference. The system 10 includes a locking or retention mechanism 600 that secures each modular cutting block to the base cutting block 12. In the illustrative embodiment, the retention mechanism 600 includes a pair of mounting brackets 602 attached to the base cutting block 12 and a corresponding pair of mounting brackets attached to each modular cutting block. The system 10 also includes a cover 604 (see FIG. 38), which may be positioned over the mounting brackets 602 of the base cutting block 12 when none of the modular cutting blocks are secured to the base cutting block 12.

Figure 23:
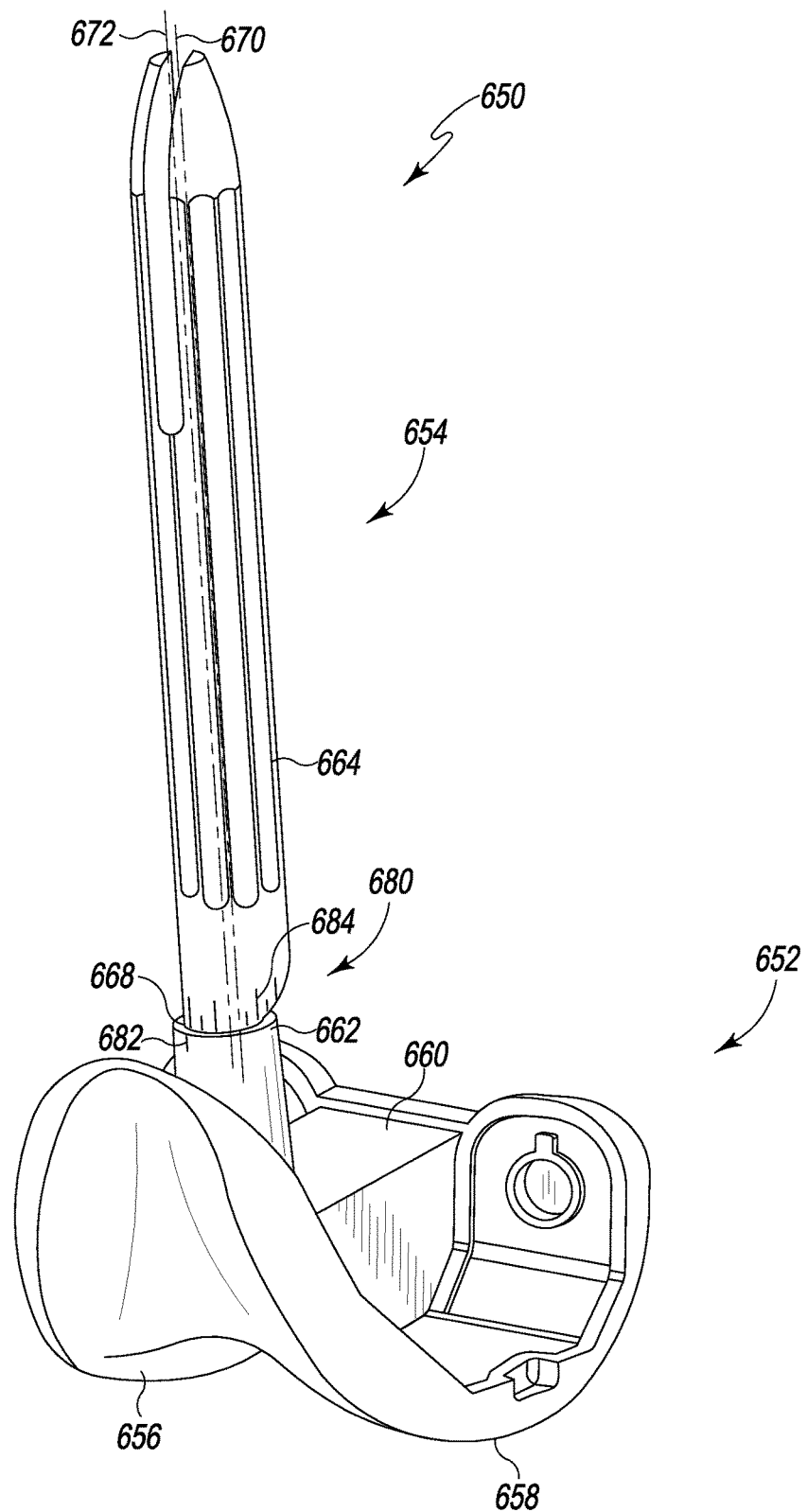
FIG. 23 is a perspective view of a femoral orthopaedic prosthesis.

Referring now to FIG. 23, a revision femoral orthopaedic prosthesis 650 for use in the performance of an orthopaedic knee replacement procedure is shown. The prosthesis 650 includes a femoral component 652 and a stem component 654 that may be secured to the femoral component 652. The components 652, 654 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic components may also be coated with a surface treatment, such as hydroxyapatite, to enhance biocompatibility. Moreover, the surfaces of the metallic components that engage the natural bone may be textured to facilitate securing the components to the bone. Such surfaces may also be porous coated to promote bone ingrowth for permanent fixation.

The femoral component 652 is configured to be implanted into a surgically-prepared distal end 622 of the patient's femur 620, and is configured to emulate the configuration of the patient's natural femoral condyles. As such, the lateral condyle surface 656 and the medial condyle surface 658 are configured (e.g., curved) in a manner which mimics the condyles of the natural femur. The lateral condyle surface 656 and the medial condyle surface 658 are spaced apart from one another thereby defining an intercondylar notch therebetween.

The condyle surfaces 656, 658 are positioned opposite a proximal surface 660. The femoral component 652 also includes an elongated stem post 662, extending superiorly away from the proximal surface 660. The elongated femoral stem post 662 is configured to receive the stem component 654.

As shown in FIG. 23, the component 654 includes an elongated body 664 that extends from a head 668. The head 668 is shaped to be received in an aperture (not shown) defined in the stem post 662. The prosthesis 650 includes a fastener (not shown) to secure the stem component 654 to the femoral component 652. The fastener may include a taper fit between the head 668 and the stem post 662, a threaded fastener, or other fastening device.

The elongated body 664 of the stem component 654 has a longitudinal axis 670 that is offset from and extends parallel to a longitudinal axis 672 of the stem post 662. As shown in FIG. 23, an oblique angle is defined between each of the axis 670, 672 and the proximal surface 660. The magnitude of that angle in the illustrative embodiment is 5 degrees. In the illustrative embodiment, the axis 670 is offset from the axis 672 by approximately 4 millimeters. It should be appreciated that in other embodiments the offset may be greater than or less than 4 millimeters depending on the patient's bony anatomy. In the illustrative embodiment, the stem component 654 may be secured to the femoral component 652 at any orientation relative about the axis 672 of the stem post 662. In that way, the elongated body 664 of the stem component 654 may be offset from the stem post 662 in any orientation about the axis 672.

The prosthesis 650 also includes an offset indicator 680 configured to indicate the offset orientation between the stem component 654 and the femoral component 652. In the illustrative embodiment, the offset indicator 680 includes a marking 682 defined on the stem post 662 and a plurality of markings 684 defined on the body 664 of the component 654. Each marking 684 corresponds to a different offset orientation. As described in greater detail below, the markings 682, 684 of the offset indicator 680 correspond to markings formed on the offset guide assembly 14 and the instrument construct 400, respectively, such that those surgical instruments may be used to determine intraoperatively the desired offset orientation of the prosthesis 650.

Figure 31:
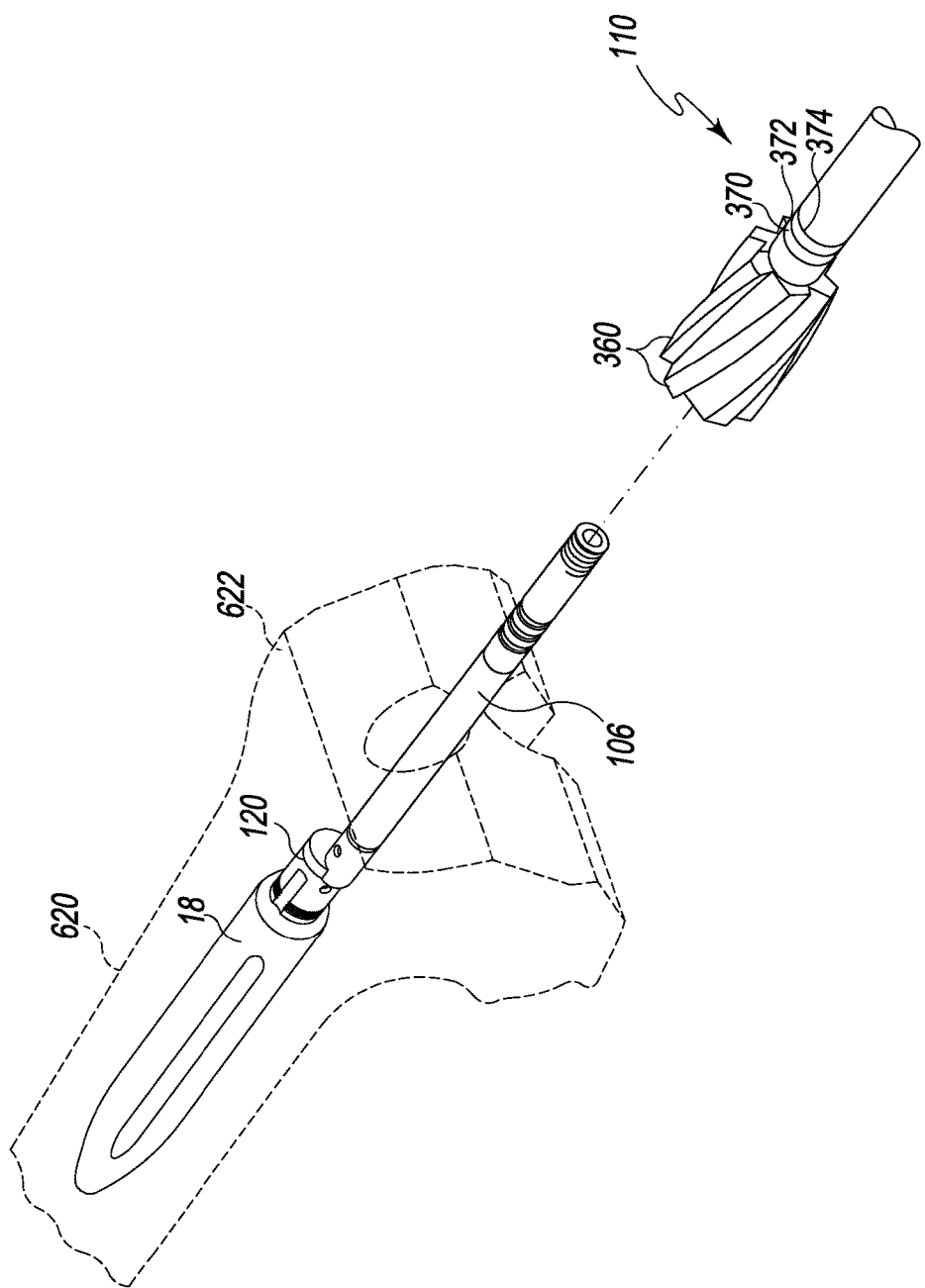
Figure 32:
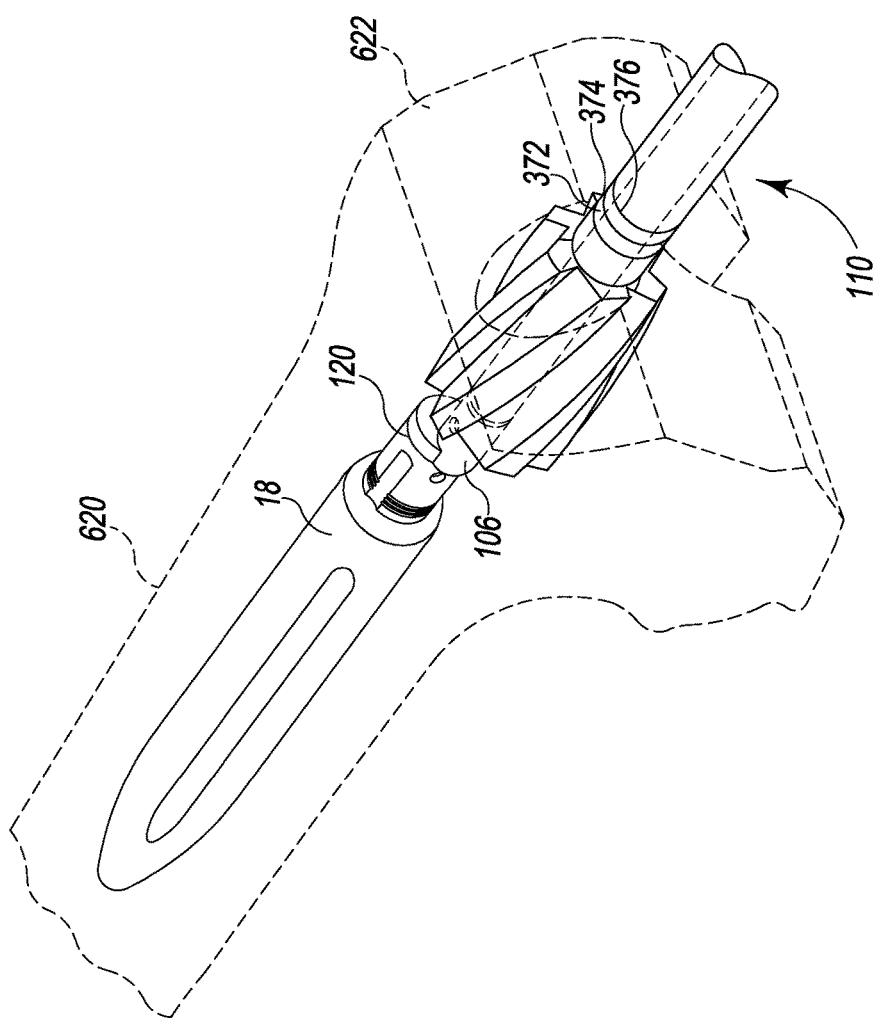
Figure 33:
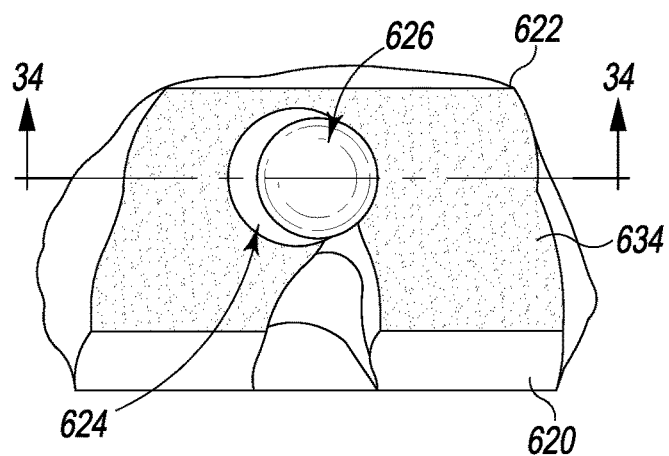
FIG. 33 is a plan view of the distal end of the patient's femur following the reaming of the distal end of the patient's femur.
Figure 34:
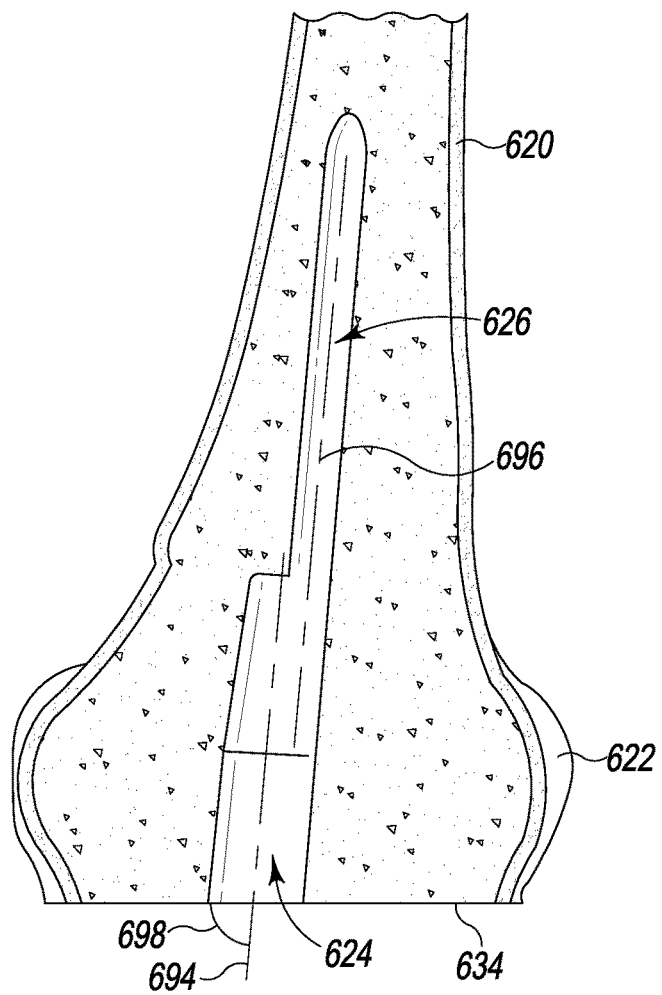
FIG. 34 is an elevation view of the patient's femur following the reaming of the distal end of the patient's femur.

As shown in FIGS. 24-39, the system 10 may be utilized during the performance of an orthopaedic surgical procedure to implant the femoral prosthesis 650 in a distal end 622 of a patient's femur 620. The offset guide assembly 14 may be utilized to plan and guide the reaming of the patient's femur 620 with the surgical reamer 110, as shown in FIGS. 24-32. As shown in FIGS. 33-34, the surgical reamer 110 forms a chamber 624 in the distal end 622 of the patient's femur 620. The chamber 624 is connected to the medullary canal 626 of the patient's femur 620 and is sized to receive the stem post 662 of the femoral component 652 and the proximal end of the stem component 654. As shown in FIGS. 35-39, the instrument construct 400 may be inserted into the chamber 624 and the medullary canal 626 and a gap assessment may be performed to determine and set femoral rotation. The construct 400 may be used to begin resecting and shaping the distal end 622 of the patient's femur 620, including the posterior surfaces 628 and the posterior chamfer surface 630, to receive the femoral prosthetic component 652.

Figure 24:
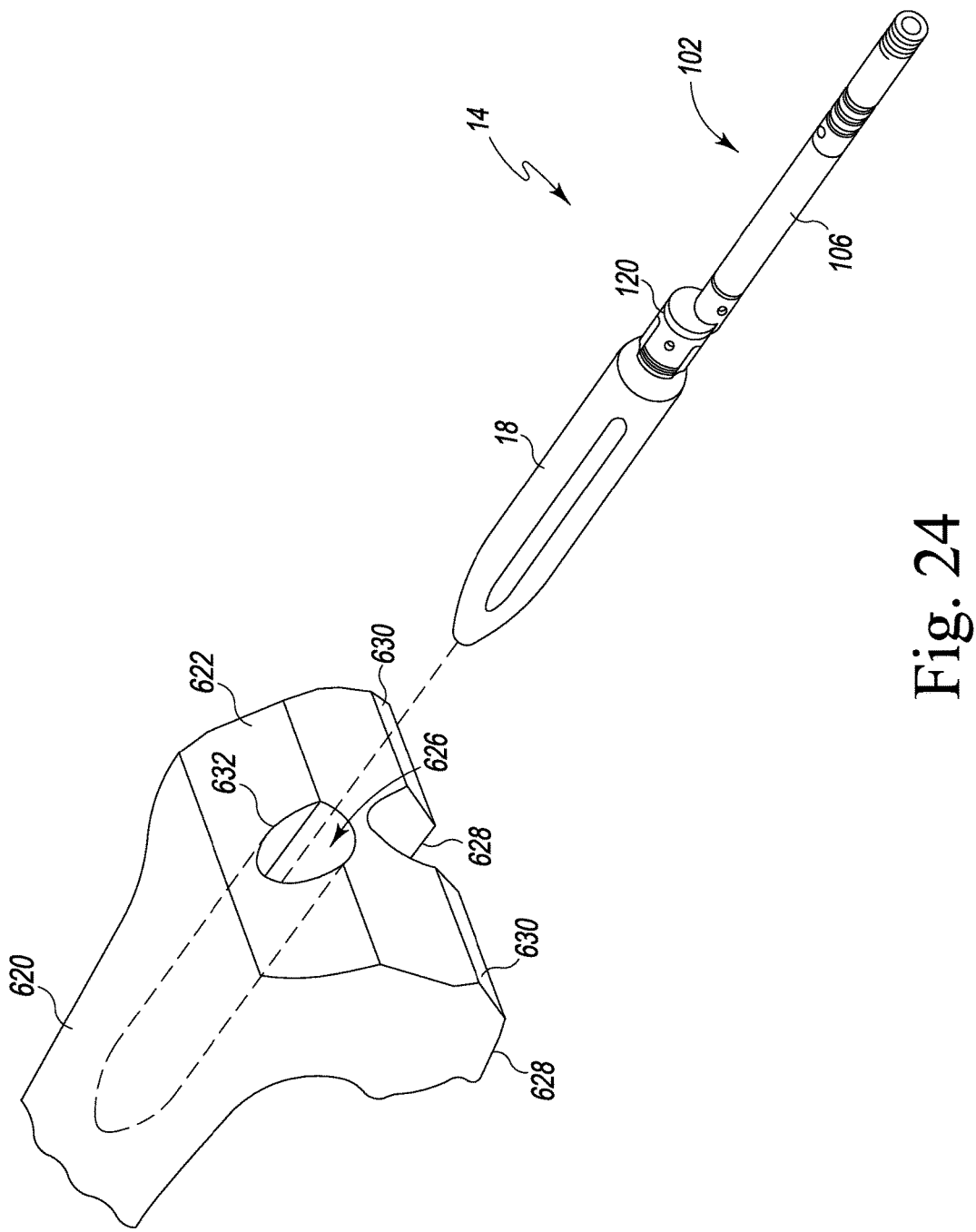
FIGS. 24-32 show the instruments of the orthopaedic surgical instrument system being used to plan and guide the reaming of the distal end of the patient's femur.

Prior to inserting the offset guide assembly 14, an orthopaedic surgeon may remove a prior prosthetic implant and drill and/or ream the medullary canal 626. Multiple drills or reamers may be used to form and/or increase the size of a distal opening 632 of the medullary canal 626 of the patient's femur 620. When the reaming operation is complete, the medullary canal 626 is configured as shown in FIG. 24.

The surgeon may utilize the offset guide assembly 14 may be utilized to determine intraoperatively a desired offset orientation of the prosthetic stem component 654 relative to the stem post 662 of the femoral component 652. To do so, the surgeon may select a stem trial 18 and secure the selected stem trial 18 to the offset guide tool 102. The stem trial 18 may be selected from a plurality of different sized stem trials 18. The stem trials may vary in length, diameter, or other aspect, and the surgeon may select the stem trial 18 based on the patient's anatomy and the type of prosthetic stem component to be included in the femoral prosthesis.

After selecting the stem trial 18, the surgeon may attach the stem trial 18 to the mounting shaft 120 of the offset guide tool 102. To do so, the surgeon may align the distal end 24 of the stem trial 18 with the passageway 130 of the shaft 120. The surgeon may then advance the distal end 24 into the passageway 130. As described above, a plurality of external threads 28 are formed on the stem trial 18, and the threads 28 engage the internal threads 30 formed on the mounting shaft 120. As such, the stem trial 18 may be threaded into the mounting shaft 120, thereby securing the stem trial 18 to the guide tool 102. As shown in FIG. 24, the assembled stem trial 18 and the guide tool 102 may be aligned with and advanced into the distal opening 632 of the medullary canal 626 of the patient's femur 620.

Figure 25:
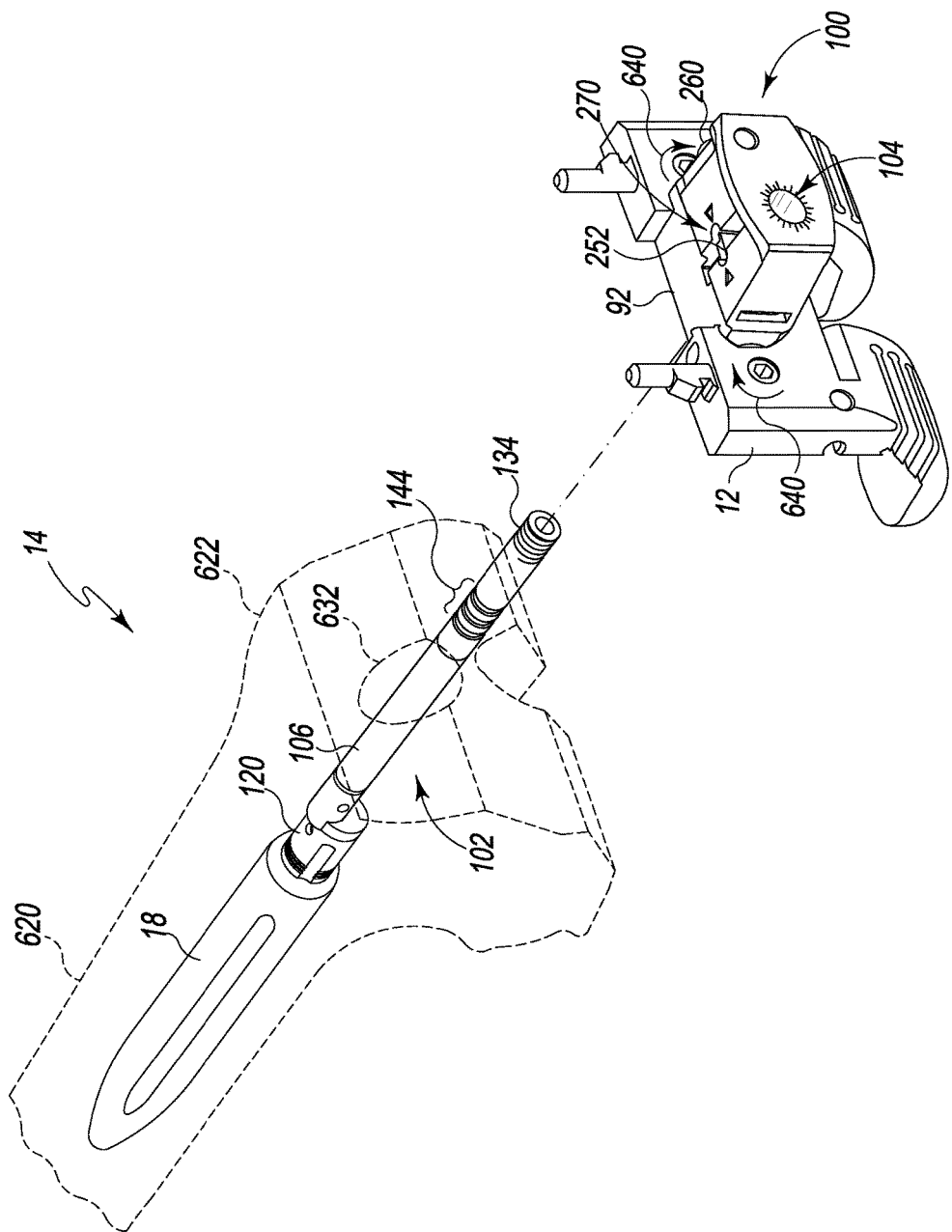

When seated in the medullary canal 626, the guide tool 102 may be coupled to the guide block 100 of the offset guide assembly 14. As shown in FIG. 25, the guide block 100 may be first secured to the base cutting block 12. To do so, the mounting bracket 92 of the guide block 100 is positioned in the receiving slot 52 of the base cutting block 12. A surgeon may use a driver or other surgical tool to rotate the locking tabs 82, 84 as indicated by arrows 640 in FIG. 25. As the locking tabs 82, 84 are rotated, the ears 88 are advanced into the corresponding channels 240 defined in the mounting bracket 92, thereby securing the blocks 12, 100 together.

The surgeon may then advance the assembled blocks 12, 100 over the distal end 134 of the guide shaft 106. Alternatively, the surgeon may choose to attach the guide block 100 to the base cutting block 12 after attaching the guide block 100 to the guide shaft 106. To secure the guide block 100 to the guide shaft 106, the guide block 100 (and hence cutting block 12) is positioned such that the passageway 104 is aligned with the distal end 134 of the guide shaft 106. The surgeon may depress the button 260 on the guide block 100 to move the locking plate 252 to the unlocked position and advance the guide block 100 over the distal end 134 of the guide shaft 106.

Figure 26:
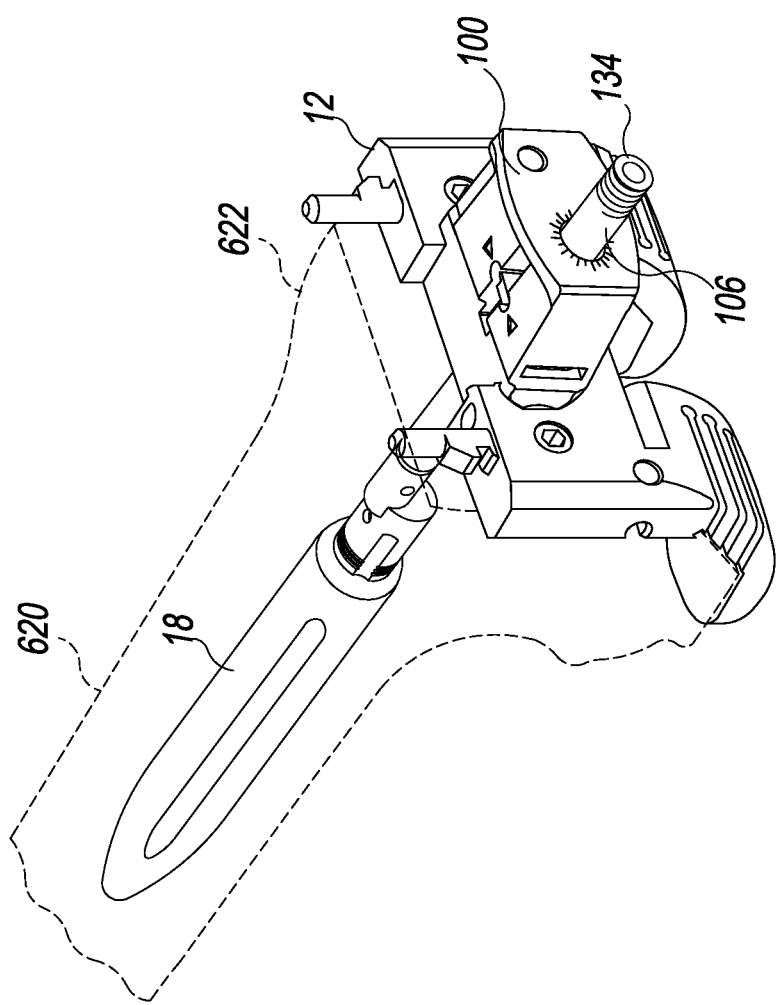

As shown in FIG. 26, the assembled blocks 12, 100 may be advanced proximally along the shaft 106 to align the block 100 with one of the slots 144 defined in the shaft 106. As described above, each slot 144 defined on the shaft 106 corresponds to a different reaming depth, and the surgeon may select the slot 144 corresponding to the reaming depth required for the selected prosthesis 650. The surgeon may utilize the window 270 defined in the guide block 100 to read the marking 148 associated with each slot 144 to identify the slot corresponding to the desired reaming depth. When the marking 148 associated with the selected slot 144 is positioned in the window 270, the surgeon may release the button 260 to permit the locking plate 252 to advance into the selected slot 144 and thereby secure the blocks 12, 100 to the guide shaft 106.

Figure 27:
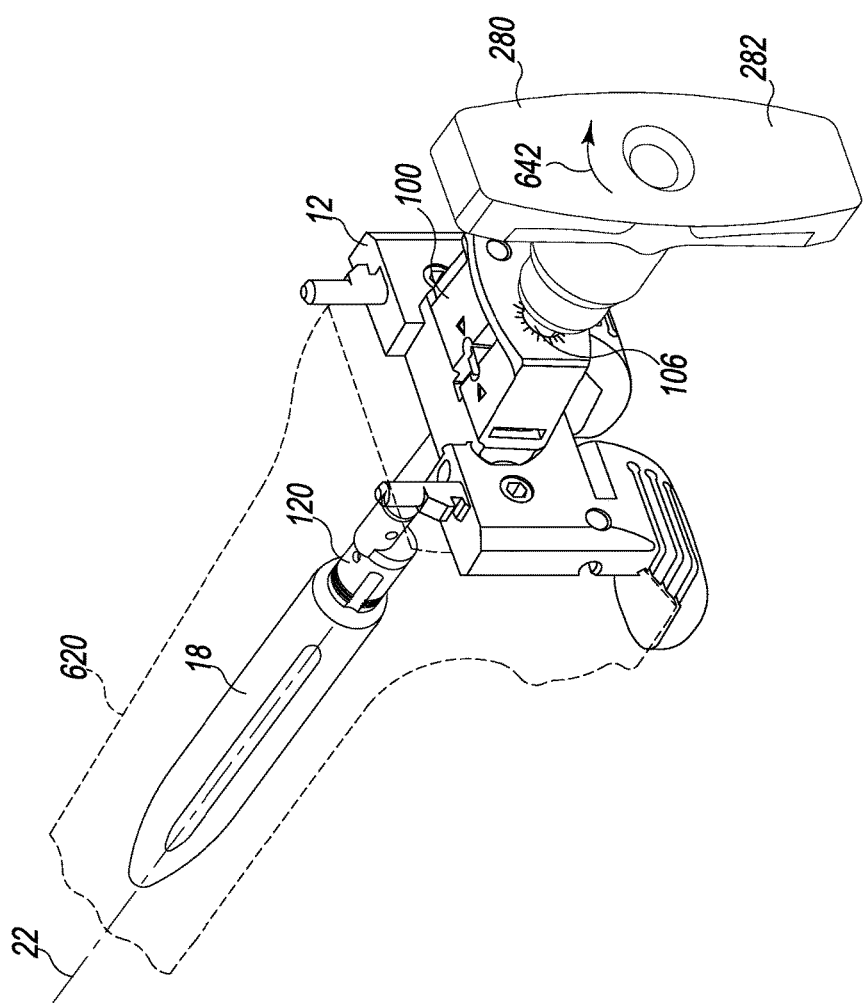

The surgeon may then attach the handle assembly 280 to the distal end 134 of the guide shaft 106, as shown in FIG. 27. To do so, the proximal passageway 322 of the handle assembly 280 is aligned with the distal end 134 and advanced over the distal end 134. The handle assembly 280 may be rotated relative to the guide shaft 106 such that the internal threads 140 of the handle assembly 280 engage the external threads 138 formed on the distal end 134 of the guide shaft 106 to secure the handle assembly 280 to the offset guide tool 102.

When the handle assembly 280 is secured to the guide shaft 106, the surgeon may utilize the handle assembly 280 to identify the desired offset orientation of the prosthesis 650. To do so, the surgeon may grip the elongated grip 282 of the handle assembly 280 to rotate the grip 282 (and hence the guide shaft 106) as indicated in FIG. 27 by arrow 642. As the grip 282 is turned, the guide shaft 106 of the guide tool 102 is rotated relative to the stem trial 18 and the mounting shaft 120 about the longitudinal axis 22 of the stem trial 18. Because the blocks 12, 100 are attached to the mounting shaft 120, the blocks 12, 100 are rotated with mounting shaft 120.

Figure 29:
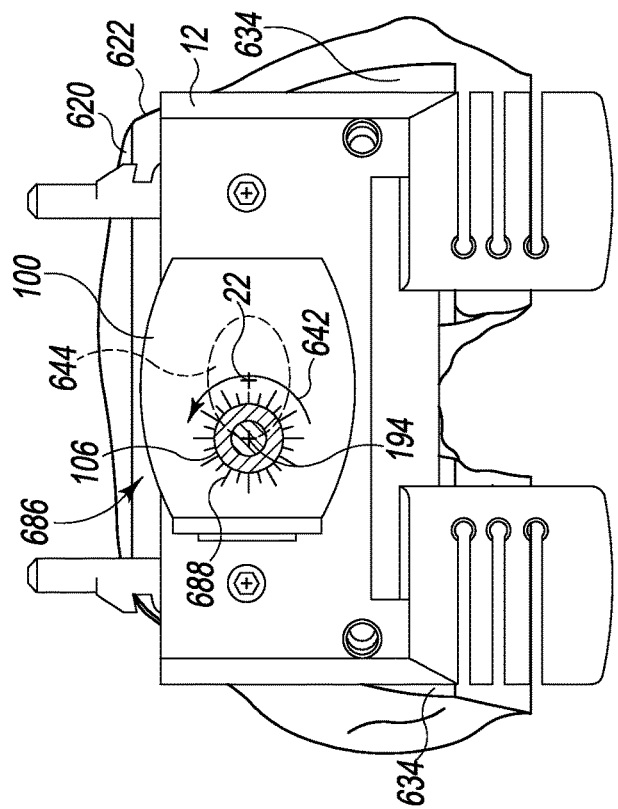
Figure 28:
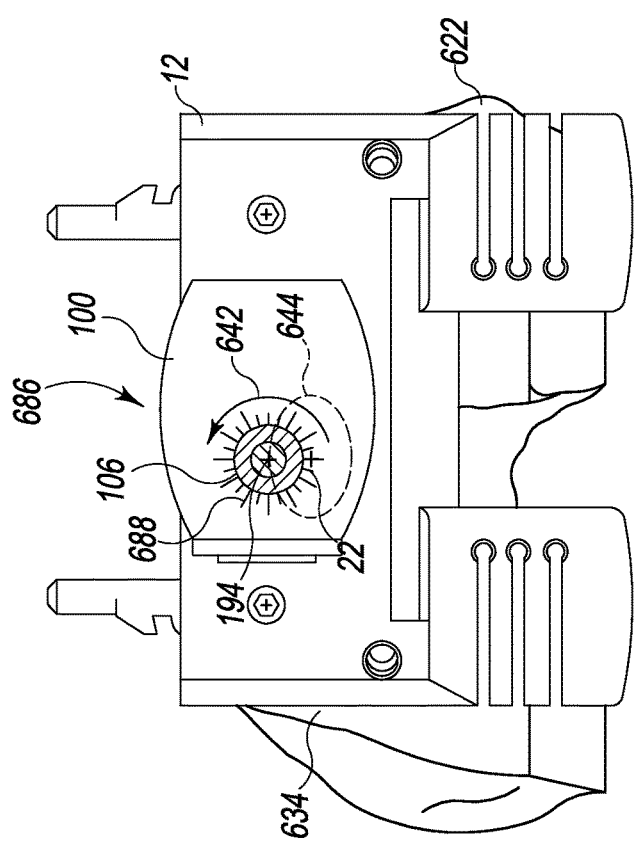

When viewed in a transverse plane defined by the distal surfaces 634 of the femur 620, as shown in FIGS. 28-29, the longitudinal axis 194 of the guide shaft 106 is moved along an elliptical path 644. That movement changes the position of the cutting block 12 on the distal end 622 of the patient's femur 620. The surgeon may continue to turn the grip 282 until the cutting block 12 is placed in a location on the patient's femur 620 that offers maximum coverage of the distal end 622. When the cutting block 12 is in the desired location on the patient's femur 620, the surgeon may utilize an offset indicator 686 on the offset guide assembly 14 to identify the selected offset orientation.

As shown in FIGS. 28-29, the offset indicator 686 includes a plurality of markings 688 defined on the proximal surface 690 of the guide block 100. Each marking 688 corresponds to a different offset orientation. In the illustrative embodiment, the markings 688 include lines and, in some embodiments, numerical indicators that are associated with the lines to identify the offset orientations. The offset indicator 686 also includes a marking 694 (see FIG. 5) on the guide shaft 106. When the marking 694 is aligned with one of the marking lines 688, the surgeon may identify the line 688 to determine the offset orientation.

Figure 30:
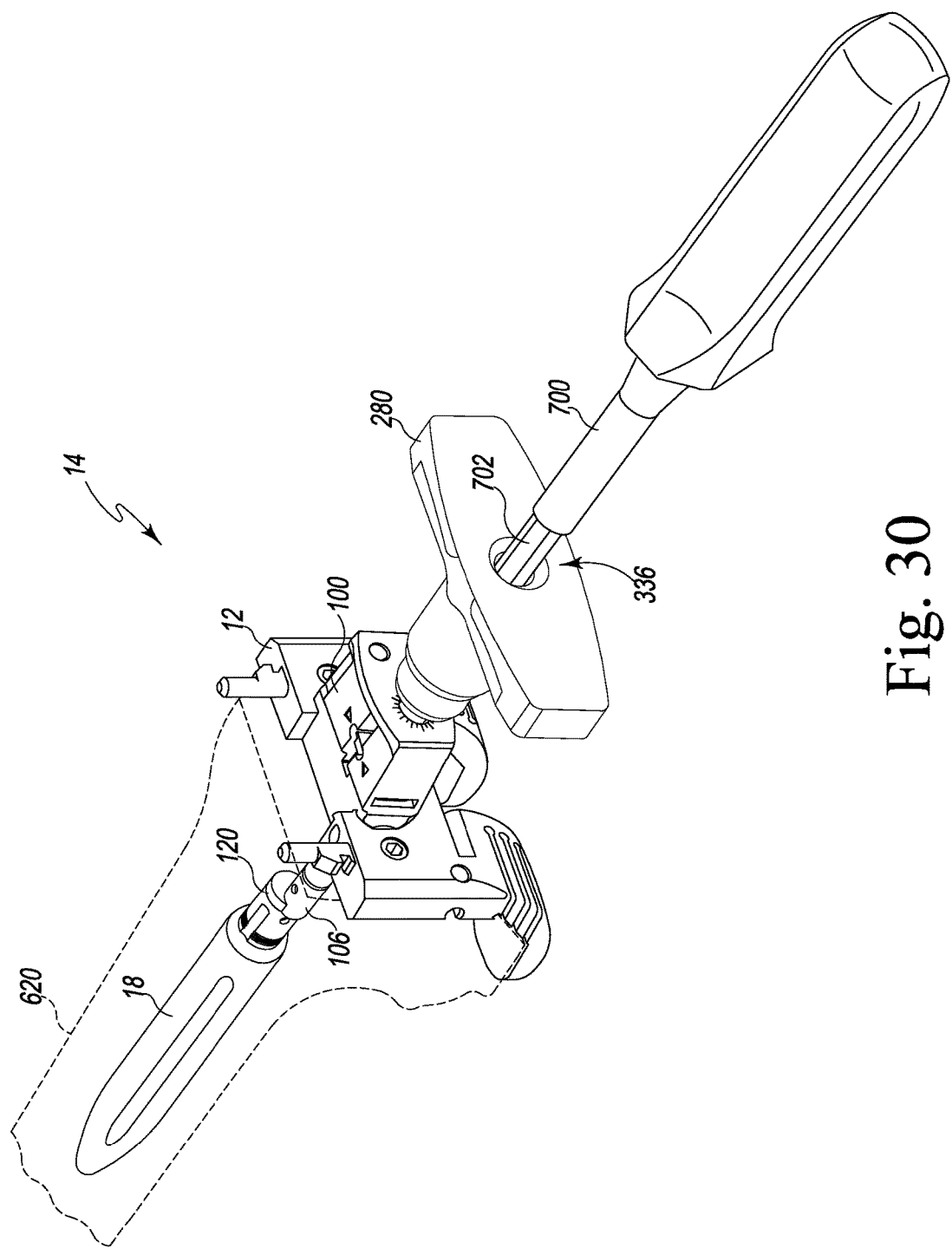

When the cutting block 12 is in the desired location on the patient's femur 620, the surgeon may lock the guide shaft 106 in position relative to the mounting shaft 120. To do so, a driver head 702 of a surgical instrument 700 may be advanced into the passageway 336 of the handle assembly 280, as shown in FIG. 30. With the driver head 702 positioned in the socket 334 of the connecting shaft 290, the connecting shaft 290 is advanced along the distal passageway 316 of the handle assembly 280 into the passageway 162 of the guide shaft 106 and engagement with the rod 202 of the guide tool locking mechanism 200.

The connecting shaft 290 may then be rotated to move the rod 202 from the unlocked position to the locked position. As described above, when the rod 202 is in the locked position, the tip 216 of the rod 202 engaged with the outer wall 222 of the mounting shaft 120, thereby preventing relative movement between the mounting shaft 120 and the connecting body 122 (and hence the guide shaft 106). When the rod 202 is in the locked position, the driver head 702 may be withdrawn from the connecting shaft 290 and the blocks 12, 100 detached from the guide shaft 106.

The surgeon may then ream the distal end 622 of the patient's femur 620 to the desired reaming depth. As shown in FIG. 31, the aperture 368 of the reamer 110 may be aligned with the distal end 134 of the guide shaft 106. The reamer 110 may then be advanced over the guide shaft 106 and into engagement with the distal end 622 of the femur 620. The reamer 110 may be attached to a rotary source such as, for example, a surgical drill configured to rotate the reamer 110. When rotated, the cutting flutes 360 of the reamer 110 engage the femur 620 to remove material from the bone. The surgeon may advance the reamer 110 proximally along the shaft 106 until one of the depth marks 370, 372, 374 of the reamer 110 is aligned with distal surfaces 634 of the patient's femur 620, as shown in FIG. 32. As described above, the depth mark is selected based on the reaming depth required to implant the revision femoral prosthesis 650. After advancing the reamer 110 to the desired depth, the reamer 110, the guide tool 102, and the stem trial 18 may be removed from the distal end 622 of the patient's femur 620.

As shown in FIGS. 33-34, the reaming operation forms a chamber 624 in the distal end 622 of the patient's femur 620. The chamber 624 is connected to the medullary canal 626 of the patient's femur 620 and is sized to receive the stem post 662 of the femoral component 652 and the proximal end of the stem component 654. As shown in FIG. 34, the chamber 624 has a longitudinal axis 694 that is offset from the anatomical axis 696 of the medullary canal 626. An oblique angle 698 is defined between the axis 694 and an imaginary plane defined by the distal surfaces 634 of the patient's femur 620.

After reaming the distal end 622 of the patient's femur 620, the surgeon may assemble the instrument construct 400 and insert the intramedullary orthopaedic surgical instrument 16 into the chamber 624 and the medullary canal 626 of the patient's femur 620. To assemble the construct 400, the surgeon selects a stem stabilizer 404 from a plurality of stem stabilizers, including stem stabilizers that have fins. The stem stabilizer may be selected based on the patient's anatomy and whether additional stability may be needed in the patient's femur 620. When the surgeon has selected an appropriate stem stabilizer 404, the surgeon may thread the stem trial 18 onto the stem stabilizer 404 to form the intramedullary orthopaedic surgical instrument 16 shown in FIG. 35.

To secure the intramedullary orthopaedic surgical instrument 16 to the intramedullary adaptor 402, the passageway 412 of the stem stabilizer 404 is aligned with the proximal end 472 of the adaptor 402. The stem stabilizer may then be advanced over the proximal end 472 and threaded onto the adaptor 402. The engagement between the threads 416, 418 of the adaptor 402 and the stabilizer 404, respectively, secures the stabilizer 404 to the adaptor 402.

The intramedullary adaptor 402 may be then attached to the base cutting block 12. To do so, the mounting bracket 440 of the adaptor 402 is positioned in the receiving slot 52 of the base cutting block 12. A surgeon may use a driver or other surgical tool to rotate the locking tabs 82, 84. As the locking tabs 82, 84 are rotated, the ears 88 are advanced into the corresponding channels 240 defined in the mounting bracket 440, thereby securing the adaptor 402 to the block 12. The surgeon may choose to attach the adaptor 402 to the base cutting block 12 before attaching the intramedullary orthopaedic surgical instrument 16 to the adaptor 402.

The surgeon may then configure the adaptor 402 to position the intramedullary orthopaedic surgical instrument 16 in the desired offset orientation. To do so, the surgeon may utilize an offset indicator 710 defined on the adaptor 402. In the illustrative embodiment, the offset indicator 710 includes a marking 712 defined on the intermediate adaptor body 444 and a plurality of markings 714 defined on the proximal adaptor body 442. Each marking 714 corresponds to one of the markings 684 on the prosthesis 650 and hence to a different offset orientation of the prosthesis 650. In the illustrative embodiment, the marking 712 is arrow-shaped, and the markings 714 include lines and, in some embodiments, numerical indicators associated with the lines to identify the offset orientations. When the marking 712 is aligned with one of the marking lines 714, the surgeon may identify the line 714 to determine the offset orientation.

As described above, the desired offset orientation is determined prior to the reaming operation using the offset guide assembly 14. The surgeon may locate the line 714 on the proximal adaptor body 442 corresponding to the offset orientation identified using the offset guide assembly 14 and rotate the intermediate adaptor body 444 (and hence the mounting bracket 440) relative to the proximal adaptor body 442 to align the marking 712 with the identified line 714. As described above, when the proximal adaptor body 442 is held fixed, the intermediate adaptor body 444 (and hence the mounting bracket 440) may be rotated about the longitudinal axis 452 of the proximal adaptor body 442.

When the intermediate adaptor body 444 is in the desired orientation relative to the proximal adaptor body 442 (and hence the intramedullary orthopaedic surgical instrument 16), the surgeon may operate the proximal locking mechanism 572. To do so, the surgeon advances a driver head through the mounting bracket into the socket 196 defined in the locking pin 534. When the pin 534 is rotated, the elongated shaft 594 of the pin 534 is advanced proximally along the bore 528 defined in the adaptor body 444 and into engagement with the distal end 470 of the proximal adaptor body 442. The engagement between the pin 534 and the proximal adaptor body 442 prevents movement between the adaptor bodies 442, 444, thereby locking the adaptor bodies 442, 444 in the desired offset orientation.

Figure 35:
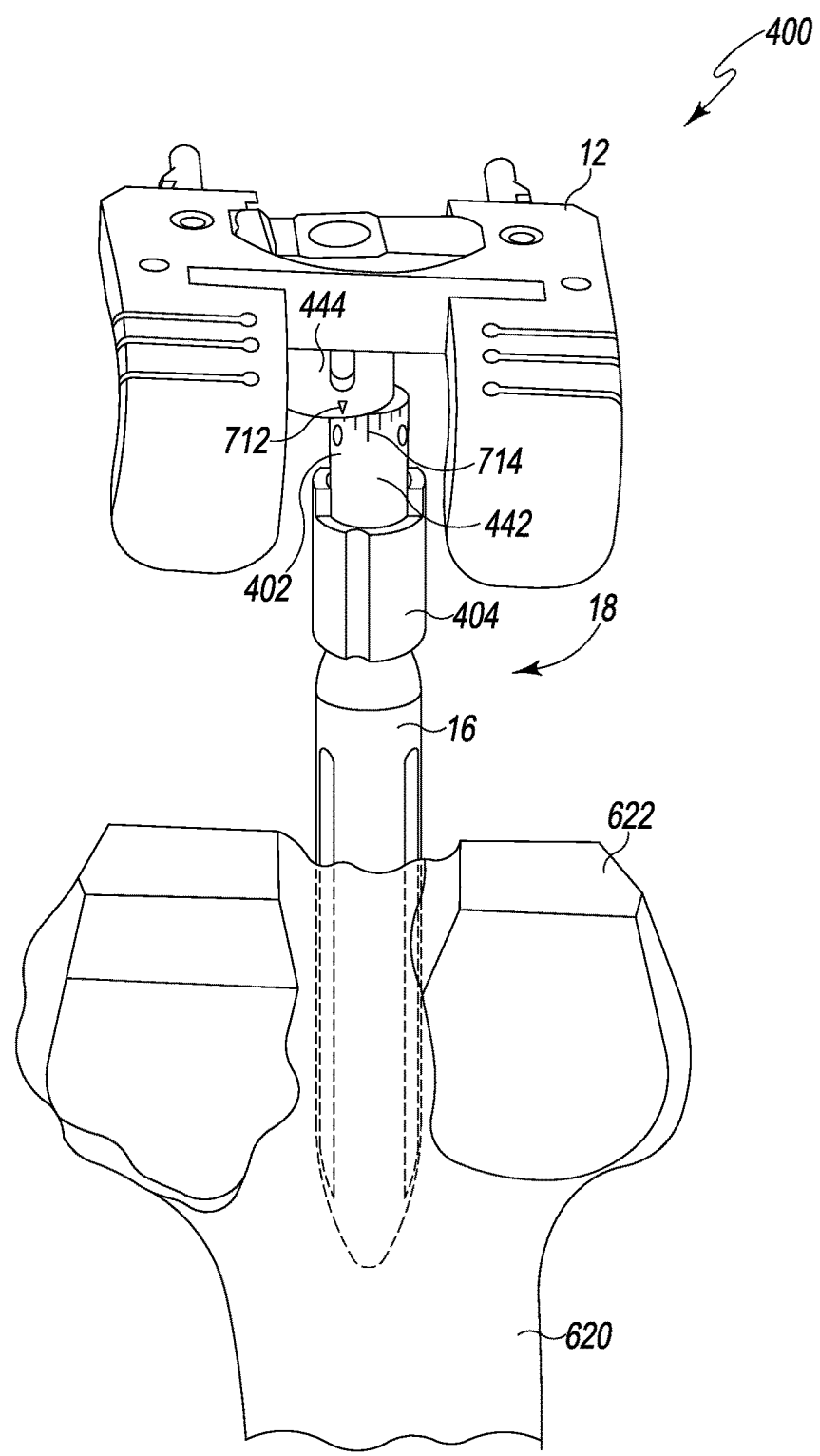
FIGS. 35-39 show the instruments of the orthopaedic surgical instrument system being used to position the cutting block of FIG. 1 on the distal end of the patient's femur and intraoperatively evaluate the joint space of the patient's knee.
Figure 36:
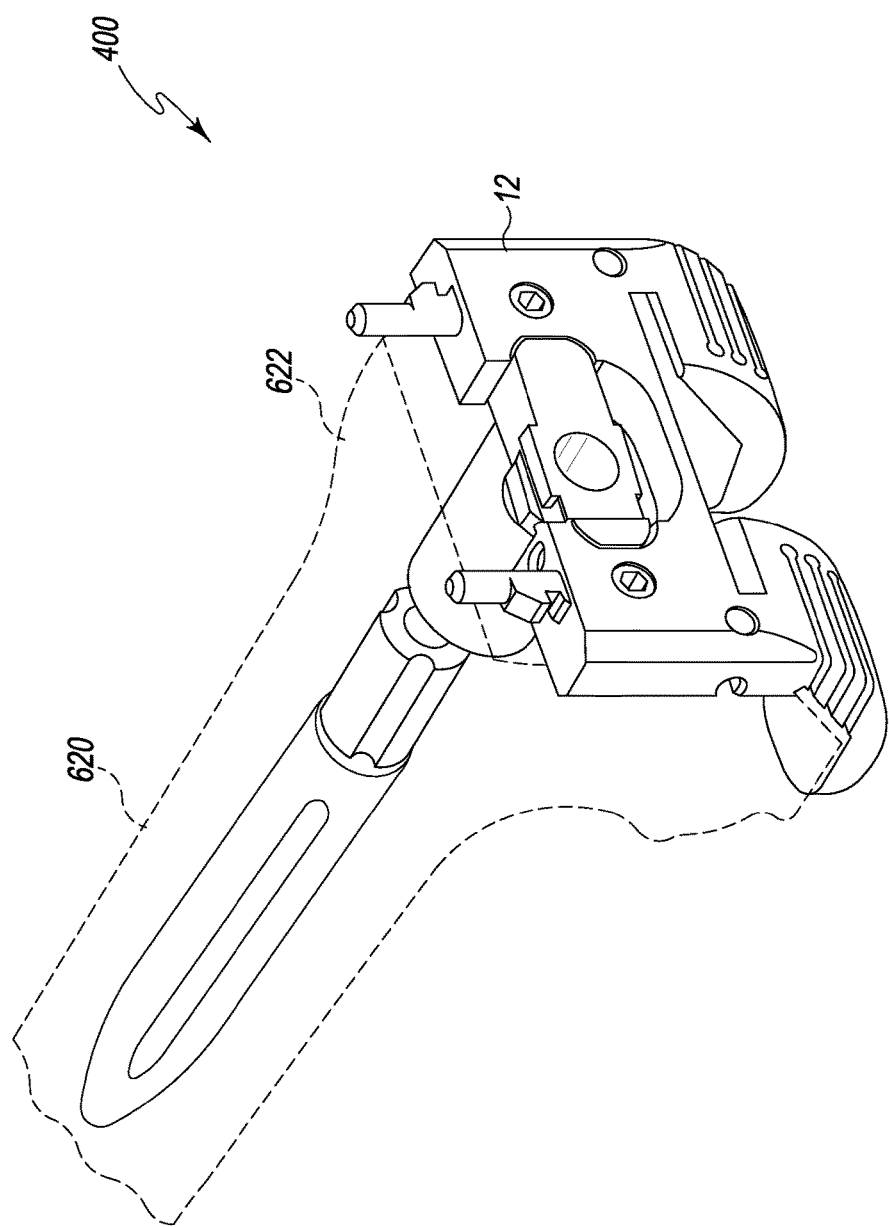

After the instrument construct 400 is assembled, the surgeon may insert the intramedullary orthopaedic surgical instrument 16 into the chamber 624 and the medullary canal 626 of the patient's femur 620. To do so, the surgeon aligns the stem trial 18 of the intramedullary orthopaedic surgical instrument 16 with the chamber 624 and advances the instrument construct 400 into the patient's femur 620, as shown in FIGS. 35-36. A mallet or other surgical tool may be used to drive the intramedullary orthopaedic surgical instrument 16 deeper into the patient's bone to the position shown in FIG. 36.

Figure 37:
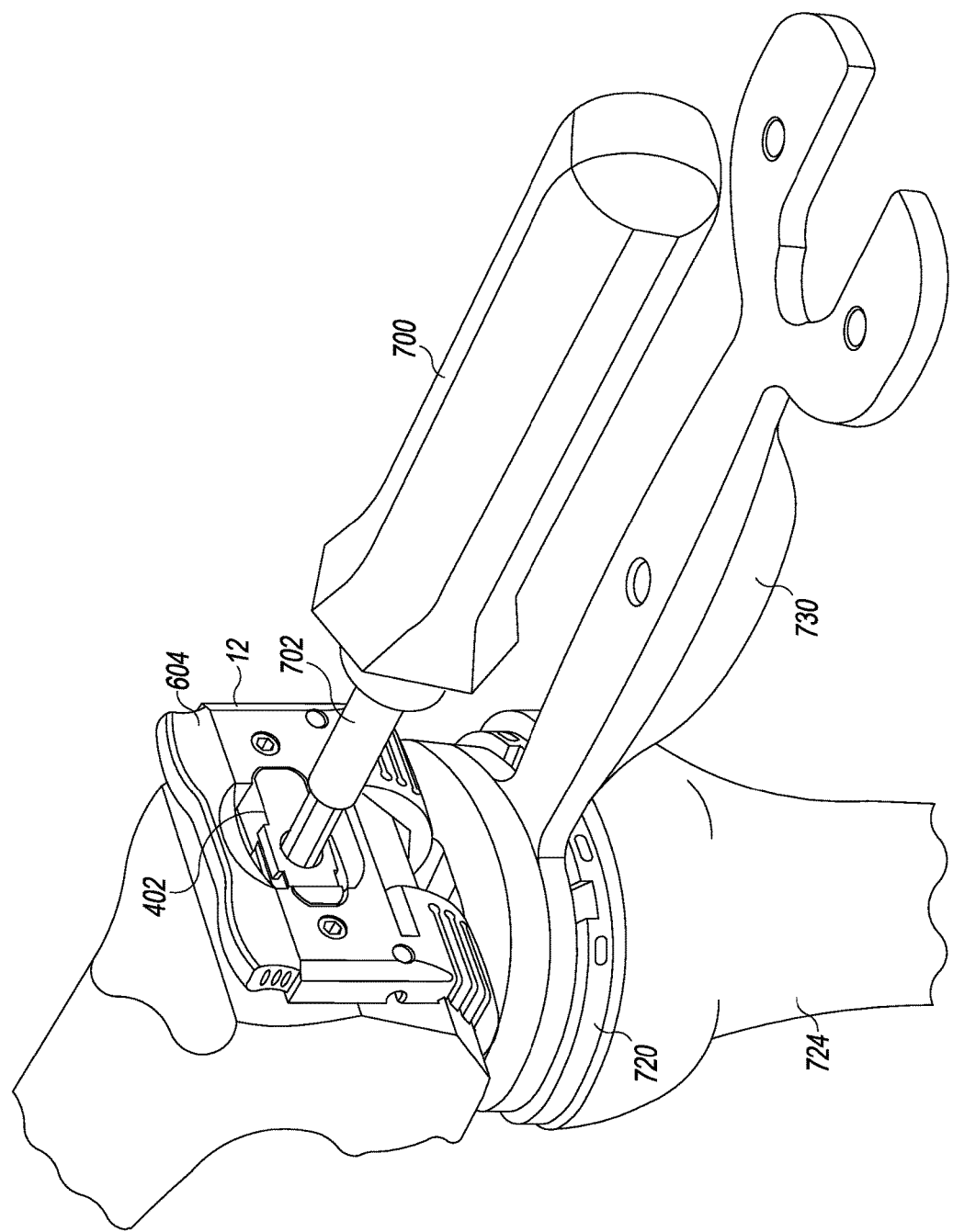
Figure 38:
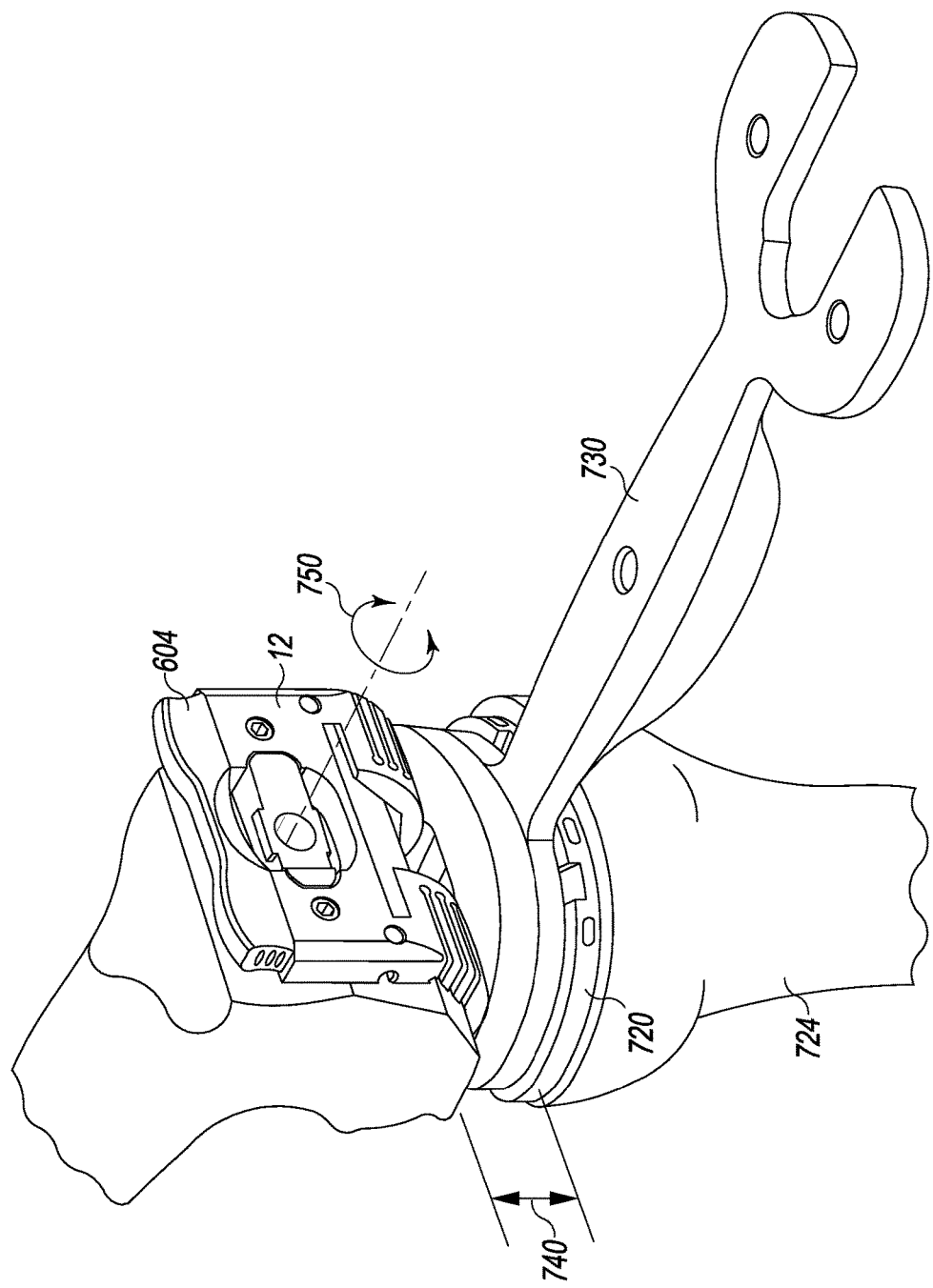
Figure 39:
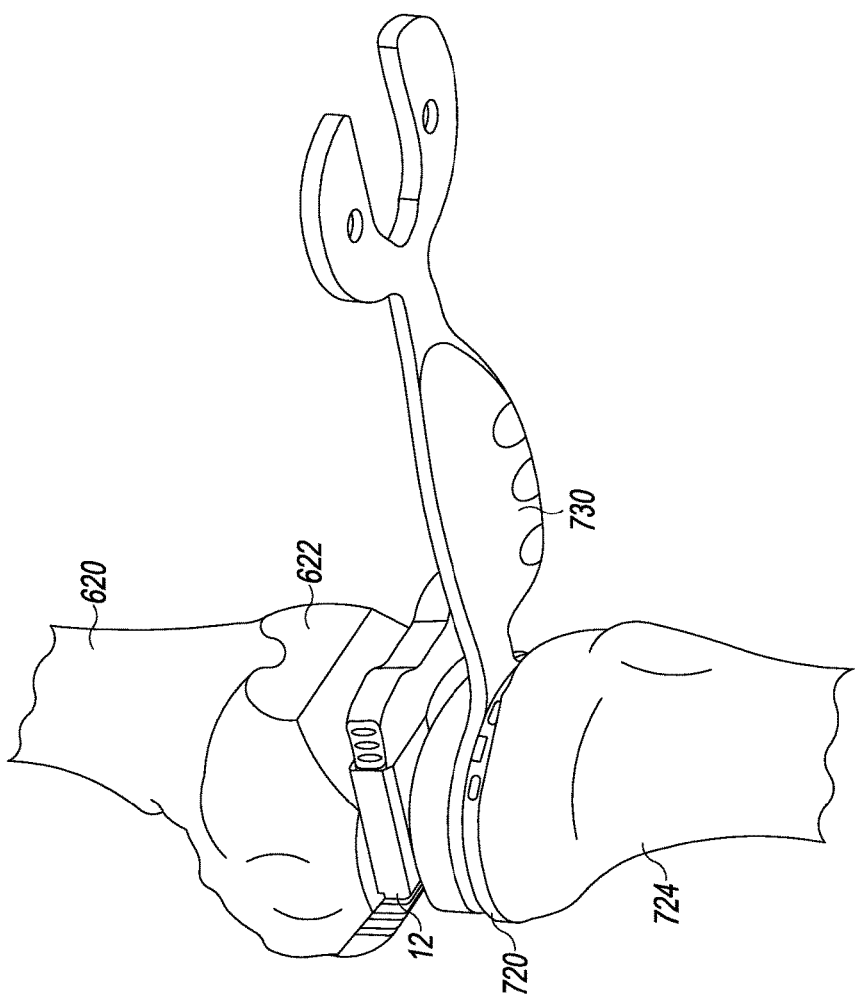

As shown in FIGS. 37-39, the surgeon may then assess the gap defined between the cutting block 12 and a tibial component 720 such as, for example, a prosthetic tibial tray or tibial tray trial. To do so, the surgeon may insert the driver head 702 of the surgical instrument 700 into the adaptor 402 to engage the socket 590 of the distal locking mechanism 570. The surgeon may rotate the driver head 702 in the direction indicated in FIG. 37 by arrow 722 to rotate the insert 524 and disengage the annular flange 586 of the adaptor body 444 from the central housing 448 of the adaptor 402. In that way, the mounting bracket 440 and the base cutting block 12 may be permitted to rotate relative to the intramedullary orthopaedic surgical instrument 16. The surgeon may also attach the cover 604 to the base cutting block 12 to cover the mounting bracket 602, as shown in FIG. 37.

The surgeon may assess the flexion and extension gaps through the range of motion. To do so, the surgeon may utilize a gap assessment tool 730 to perform the assessment. An exemplary gap assessment tool is shown and described in U.S. patent application Ser. No. 13/485,470 entitled "FEMORAL ORTHOPAEDIC SURGICAL INSTRUMENTS AND METHOD OF USE OF SAME," which is incorporated herein by reference.

As shown in FIG. 38, a gap 740 is defined between the base cutting block 12 and a tibial trial component 720 attached to a patient's tibia 724. With the patient's knee in flexion as shown in FIG. 38, the surgeon may insert the gap assessment tool 730 into the gap 740. The surgeon may move the knee between flexion (FIG. 38) and extension (FIG. 39) to evaluate the gap 740 and the stability of the construct throughout the range of motion. The surgeon may adjust the thickness of the assessment tool 730 to achieve desired gap geometry. It should be appreciated that in other embodiments the gap assessment may be performed with another type of tensioning device, such as, for example, a laminar spreader.

The surgeon may also consider the femoral rotation of the base cutting block 12. To do so, the surgeon may balance the base cutting block 12 parallel to the tibial component 720 at 90 degrees of flexion as shown in FIG. 38. The surgeon may grasp the side walls 54 of the base cutting block 12 to rotate the base cutting block 12 in the direction indicated by arrows 750 until the gap 740 defined between the base cutting block 12 and the tibial component 720 is rectangular. When the base cutting block 12 is balanced, the surgeon may use the driver head 702 to operate the distal locking mechanism 570 to secure the intramedullary adaptor 402 to the intramedullary orthopaedic surgical instrument 16, thereby preventing relative movement between the mounting bracket 440 and the base cutting block 12 and the instrument 16.

When the instrument construct 400 is properly positioned relative to the distal end 622 of the patient's femur 620, the surgeon may proceed with further resections to shape the distal end 622 to receive the prosthetic femoral component 652. To do so, the surgeon may attach one or more modular cutting blocks to the base cutting block 12. The surgeon may also use the cutting guides 76, 78 to guide posterior and chamfer cuts of the distal end 622 of the patient's femur 620.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument system comprising:
a femoral cutting block including a plurality of cutting guides sized to receive and guide a cutting saw blade to resect portions of a distal end of a patient's femur, each cutting guide of the plurality of cutting guides extending parallel to the other cutting guides of the plurality of cutting guides through a curved outer surface,
an offset adaptor assembly comprising:
(i) a mounting bracket configured to be coupled to the femoral cutting block,
(ii) an intermediate body pivotally coupled to the mounting bracket and having a first longitudinal axis, and
(iii) a proximal body pivotally coupled to the intermediate body and having a second longitudinal axis that is spaced apart from the first longitudinal axis,
a stem stabilizer coupled to the proximal body and extending along the second longitudinal axis, and
a stem trial coupled to the stem stabilizer, the stem trial including an elongated body that extends along the second longitudinal axis to a proximal tip,
wherein the mounting bracket has a distal-most surface that defines a plane, and an oblique angle is defined between the first longitudinal axis and the plane.

2. The orthopaedic surgical instrument system of claim 1, wherein the first longitudinal axis extends parallel to the second longitudinal axis.

3. The orthopaedic surgical instrument system of claim 1, wherein the mounting bracket has an opening, and the intermediate body includes a distal end positioned within the opening.

4. The orthopaedic surgical instrument system of claim 3, wherein a cavity is defined in the distal end of the intermediate body, the cavity being sized to receive a surgical tool.

5. An orthopaedic surgical instrument system comprising:
a femoral cutting block including a plurality of cutting guides sized to receive and guide a cutting saw blade to resect portions of a distal end of a patient's femur, each cutting guide of the plurality of cutting guides extending parallel to the other cutting guides of the plurality of cutting guides through a curved outer surface,
an offset adaptor assembly comprising:
(i) a mounting bracket configured to be coupled to the femoral cutting block,
(ii) an intermediate body pivotally coupled to the mounting bracket and having a first longitudinal axis, and
(iii) a proximal body pivotally coupled to the intermediate body and having a second longitudinal axis that is spaced apart from the first longitudinal axis,
a stem stabilizer coupled to the proximal body and extending along the second longitudinal axis, and
a stem trial coupled to the stem stabilizer, the stem trial including an elongated body that extends along the second longitudinal axis to a proximal tip, wherein:
the stem stabilizer includes a threaded bore, and
the proximal body includes a threaded end operable to be threaded within the threaded bore of the stem stabilizer.

6. An orthopaedic surgical instrument system comprising:
a femoral cutting block including a plurality of cutting guides sized to receive and guide a cutting saw blade to resect portions of a distal end of a patient's femur, each cutting guide of the plurality of cutting guides extending parallel to the other cutting guides of the plurality of cutting guides through a curved outer surface,
an offset adaptor assembly comprising:
(i) a mounting bracket configured to be coupled to the femoral cutting block,
(ii) an intermediate body pivotally coupled to the mounting bracket and having a first longitudinal axis, and
(iii) a proximal body pivotally coupled to the intermediate body and having a second longitudinal axis that is spaced apart from the first longitudinal axis,
a stem stabilizer coupled to the proximal body and extending along the second longitudinal axis, and
a stem trial coupled to the stem stabilizer, the stem trial including an elongated body that extends along the second longitudinal axis to a proximal tip, wherein:
the stem stabilizer includes a threaded bore, and
the stem trial includes a threaded distal end operable to be threaded within the threaded bore of the stem stabilizer.

* * * * *